(12) United States Patent
Seong et al.

(10) Patent No.: US 8,324,246 B2
(45) Date of Patent: Dec. 4, 2012

(54) INDOL CARBOXYLIC ACID BISPYRIDYL CARBOXAMIDE DERIVATIVES, PHARMACEUTICALLY ACCEPTABLE SALT THEREOF, PREPARATION METHOD AND COMPOSITION CONTAINING THE SAME AS AN ACTIVE INGREDIENT

(75) Inventors: Churlmin Seong, Daejeon (KR); Chul Min Park, Daejeon (KR); Soyoung Kim, Busan (KR); Wookyu Park, Cheongju-si (KR); Nosang Park, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 740 days.

(21) Appl. No.: 12/393,528

(22) Filed: Feb. 26, 2009

(65) Prior Publication Data

US 2009/0258876 A1 Oct. 15, 2009

(30) Foreign Application Priority Data

Apr. 10, 2008 (KR) .................. 10-2008-0033284

(51) Int. Cl.
*A01N 43/40* (2006.01)
*A61K 31/445* (2006.01)
*C07D 211/30* (2006.01)
*C07D 233/00* (2006.01)

(52) U.S. Cl. .................. 514/315; 546/248; 548/300.1
(58) Field of Classification Search .................. 546/248; 514/315; 548/300.1
See application file for complete search history.

(56) References Cited

U.S. PATENT DOCUMENTS

| 2,876,235 | A | | 3/1959 | Voegtli | |
| 3,253,989 | A | | 5/1966 | Moser et al. | |
| 6,022,884 | A | * | 2/2000 | Mantlo et al. | 514/352 |
| 2007/0004677 | A1 | * | 1/2007 | Chao et al. | 514/64 |
| 2008/0293720 | A1 | * | 11/2008 | Cleary et al. | 514/237.2 |

FOREIGN PATENT DOCUMENTS

| DE | 19934433 A1 | | 1/2001 |
| EP | 0226842 | | 7/1987 |
| EP | 0863136 | | 9/1998 |
| JP | 03-161470 | * | 7/1991 |
| JP | 03161470 | | 7/1991 |
| WO | 8704928 | | 8/1987 |
| WO | WO9316081 | | 8/1993 |
| WO | WO 96/02537 | * | 2/1996 |
| WO | WO9602537 | | 2/1996 |
| WO | WO 97/48699 | * | 12/1997 |
| WO | WO 97/48700 | * | 12/1997 |
| WO | WO9748699 | | 12/1997 |
| WO | WO9748700 | | 12/1997 |
| WO | 0012482 | | 3/2000 |
| WO | 0012502 | | 3/2000 |
| WO | 0035922 | | 6/2000 |
| WO | 0044737 | | 8/2000 |
| WO | WO02051833 | | 7/2002 |
| WO | WO03076426 | | 9/2003 |

OTHER PUBLICATIONS

Bromidge et al., Bioorganic & Medicinal Chem Letters 10 (2000) 1867-1870.*
Park C M et al: "Synthesis and structure-activity relationship of 1H-indole-3-carboxylic acid pyridine-3-ylamides: A novel series of 5-HT2C receptor antagonists" Bioorganic & Medicinal Chemistry Letters, Pergamon, Elsevier Science, vol. 18, No. 14, Jul. 15, 2008, pp. 3844-3847, GB.
Bromidge S M et al: "1[2-[(Heteroarylmethoxy)aryl]carbamoyl]indolines are Selective and Orally Active 5-HT2c Receptor Inverse Agonists," Bioorganic & Medicinal Chemistry Letters 10 Jun. 21, 2000 pp. 1867-1870, UK.
Bromidge S M et al: "Biarylcarbamoylindolines Are Novel and Selective 5-HT 2c Receptor Inverse Agonists: Identification of 5-Methyl-1-[[2-[2-methyl-3-pyridyl)oxy]-5-pyridyl]carbamoyl]-6-trifluoromethylindoline (SB-243213) as a Potential Antidepressant/Anxiolytic Agent," J. Med. Chem 2000, 43 1123-1134, UK.
European Search Report for corresponding EP Application No. 09250745.8-2101, mailed Jul. 22, 2009.
Korean Examination Report for corresponding Korean Patent Application No. 9-5-2010-029984379, mailed Jul. 13, 2010.
Tecott, et al., Eating disorder and epilepsy in mice lacking 5-HT2c serotonin receptors, Nature, vol. 374(6), pp. 542-546, 1995.
Sargent, et al., 5-HT2c receptor activation decreases appetite and body weight in obese subjects, Psychopharmacology, vol. 133, pp. 309-312, 1997.

* cited by examiner

Primary Examiner — Paul V. Ward
(74) Attorney, Agent, or Firm — Lucas & Mercanti, LLP

(57) ABSTRACT

Disclosed herein are a new indole carboxylic acid bispyridyl carboxamide derivative, a preparation method thereof, and a composition for prevention or treatment of obesity, urinary disorders, and CNS disorders, containing the same as an active ingredient. Because the indole carboxylic acid bispyridyl carboxamide derivatives according to the present invention have high affinity for 5-$HT_{2c}$ receptors, act selectively on the 5-$HT_{2c}$ receptors, the derivatives rarely have adverse effects caused by other receptors. Because the derivatives effectively inhibit serotonin activity, they may be useful for treatment or prevention of obesity; urinary disorders such as urinary incontinence, premature ejaculation, erectile dysfunction, and prostatic hyperplasia; CNS disorders such as depression, anxiety, concern, panic disorder, epilepsy, obsessive-compulsive disorder, migraine, sleep disorder, withdrawal from drug abuse, Alzheimer's disease, and schizophrenia, associated with 5-$HT_{2c}$ receptors.

11 Claims, 1 Drawing Sheet

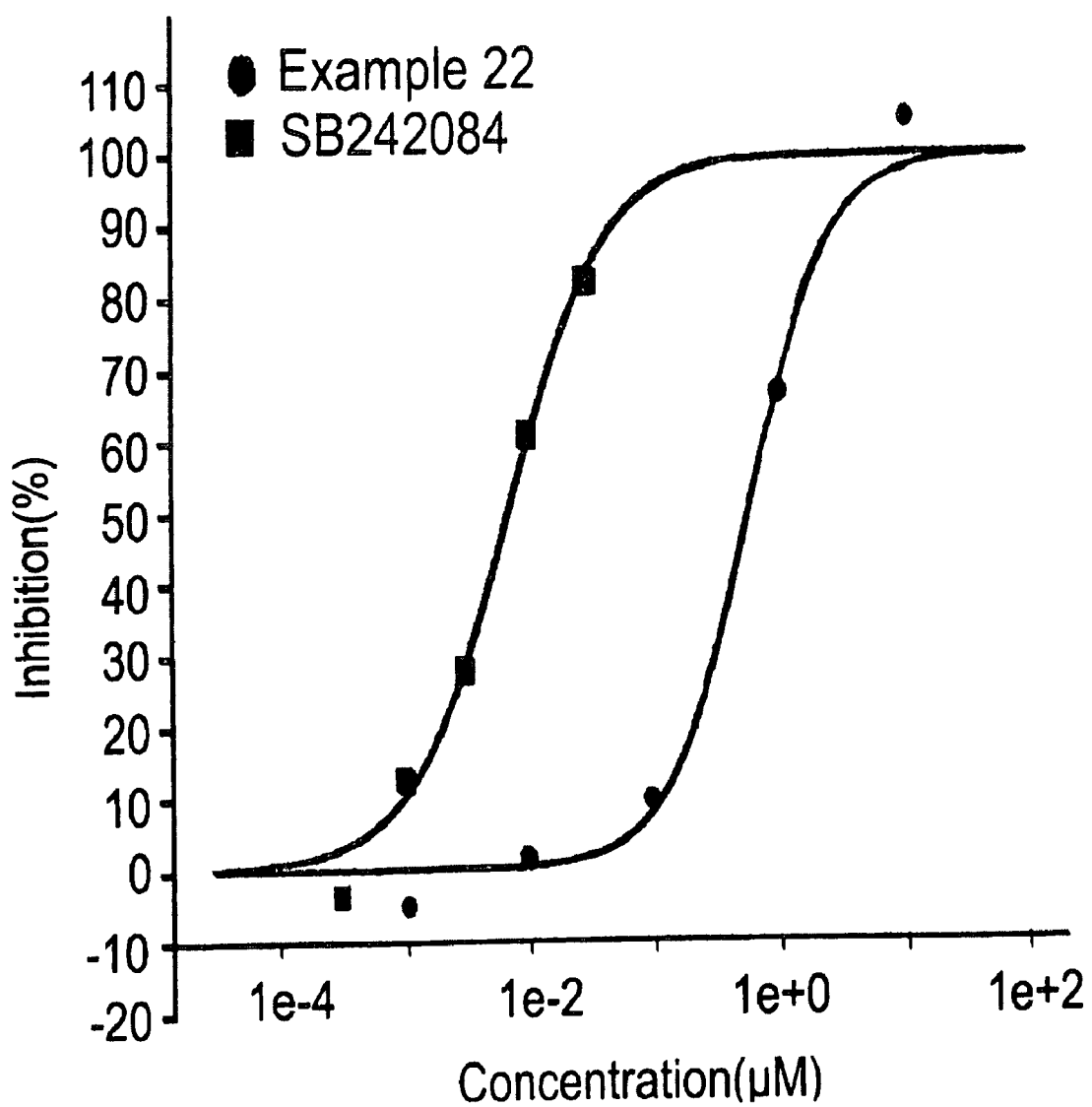

INDOL CARBOXYLIC ACID BISPYRIDYL CARBOXAMIDE DERIVATIVES, PHARMACEUTICALLY ACCEPTABLE SALT THEREOF, PREPARATION METHOD AND COMPOSITION CONTAINING THE SAME AS AN ACTIVE INGREDIENT

CROSS-REFERENCES TO RELATED APPLICATION

This patent application claims the benefit of priority under 35 U.S.C. §119 from Korean Patent Application No. 10-2008-0033284 filed Apr. 10, 2008, the contents of which are incorporated herein by reference.

TECHNICAL FIELD

The present disclosure relates to a novel indole carboxylic acid bispyridyl carboxamide derivative, a pharmaceutically acceptable salt thereof, a preparation method and a composition containing the same as an active ingredient.

BACKGROUND ART

The transmission of excitation through nerves and the actions of main organs are performed by neurotransmitters. These neurotransmitters include a cholinergic neurotransmitter system which secrets acetylcholine caused by stimuli in the central and peripheral nervous systems, and an adrenergic transmitter system which secrets noradrenaline. Besides, there are a lot of neurotransmitters considered to be important in the central nervous system (CNS), such as dopamine, serotonin, and inhibitory GABA (γ-aminobutyric acid). Among them, the serotonin nervous system is closely related to mental illnesses such as concern, anxiety, depression, and the like. It is known that the distribution of its receptors is considerably reduced in patients with mental illness or dementia. The serotonin system in the brain is known to regulate various physiological actions and mental states as an important neurotransmission network which control behaviors and physical functions including concern and emotional anxiety.

Serotonin (5-HT) in the central nervous system has been linked with cause of many diseases and is known to be responsible for, in particular, mental diseases such as depression, anxiety, schizophrenia, eating disorders, obsessive compulsive disorders (OCD), migraine, and panic disorder. Recent advances in pharmacology, molecular biology, and genetics on the serotonin nervous system have enabled the development of improved drug therapies for treatment of specific nervous system diseases. In fact, current general treatment methods for theses diseases have been considered to work by regulating physiological activities of serotonergic materials.

In the serotonin system having various receptor subtypes, serotonin receptors activated by 5-HT were revealed to have at least 7 subtypes ($5\text{-HT}_{1-7}$), which were again divided into different subtypes (A, B . . . ). The $5\text{-HT}_{2c}$ serotonin receptor subtype is transcribed and expressed in hypothalamic structure associated with appetite regulation.

It has been demonstrated that the $5\text{-HT}_{2c}$ receptor agonist m-chlorophenylpiperazine (mCPP), which has some preference for the $5\text{-HT}_{2c}$ receptor, reduces food intake in mice that express the normal $5\text{-HT}_{2c}$ receptor while the compound lacks activity in mice expressing the mutated inactive form of the $5\text{-HT}_{2c}$ receptor (Nature (1995), 374, 542-546). In a recent clinical study, a sustained reduction in body weight was obtained after 2 weeks of treatment with mCPP in obese subjects (Psychopharmacology (1997), 133, 309-312).

The $5\text{-HT}_{2c}$ receptor has been suggested to be involved in CNS disorders such as depression and anxiety (IDrugs (1999), 2, 109-120).

The $5\text{-H}_{2c}$ receptor has also been suggested to be involved in urinary disorders such as urinary incontinence (IDrugs (1998), 1, 456-470).

Compounds which have a selective effect on the $5\text{-HT}_{2c}$ receptor may therefore have a therapeutic potential in the treatment of disorders like those mentioned above. Of course, selectivity also reduces the potential for adverse effects mediated by other serotonin receptors.

The prior art for $5\text{-HT}_{2c}$ receptor antagonists is described below.

U.S. Pat. No. 3,253,989 discloses the use of mCPP as an anorectic agent.

EP-A1-863 136 discloses azetidine and pyrrolidine derivatives which are selective $5\text{-HT}_{2c}$ receptor agonists having antidepressant activity and which can be used for treating or preventing serotonin-related diseases, including eating disorders and anxiety.

WO 87/04928 discloses 2-(1-piperazinyl)pyrimidines as agents for treating neuropathy.

EP-A2-226842 discloses 1,4-naphthalenedione heterocyclic derivatives as antiallergics and antiasthmatics including 2-(3-bromophenyl)-4-(1-piperazinyl)-pyrimidine.

EP-A-657 426 discloses tricyclic pyrrole derivatives having activity on the $5\text{-HT}_{2c}$ receptor and which inter alia may be used for treating eating disorders.

EP-A-655 440 discloses 1-aminoethylindoles having activity on the $5\text{-HT}_{2c}$ receptor and which inter alia may be used for treating eating disorders.

EP-A-572 863 discloses pyrazinoindoles having activity on the $5\text{-HT}_{2c}$ receptor and which inter alia may be used for treating eating disorders.

WO 00/12475 discloses indole derivatives as $5\text{-HT}_{2b}$ or $5\text{-HT}_{2c}$ receptor ligands, especially for the treatment of obesity.

WO 00/12510 discloses pyrroloindoles, pyridoindoles and azepinoindoles as $5\text{-HT}_{2c}$ receptor agonists, particularly for the treatment of obesity.

WO 00/12482 discloses indazole derivatives as selective, directly active $5\text{-HT}_{2c}$ receptor ligands, particularly for use as anti-obesity agents.

WO 00/12502 discloses pyrroloquinolines as $5\text{-HT}_{2c}$ receptor agonists, particularly for use as anti-obesity agents.

WO 00/035922 discloses 2,3,4,4,α-tetrahydro-1H-pyrazino[1,2-α]quinoxalin-5(6H)ones as $5\text{HT}_{2c}$ agonists, which may be used for the treatment of obesity.

WO 00/044737 discloses aminoalkylbenzofurans as $5\text{-HT}_{2c}$ agonists, which may be used for the treatment of obesity.

However, there still remains a need for development of $5\text{-HT}_{2c}$ receptor antagonists having higher affinity and selectivity for $5\text{-HT}_{2c}$ receptors.

Thus, the present inventors have performed research to develop $5\text{-HT}_{2c}$ receptor antagonists having higher affinity and selectivity for $5\text{-HT}_{2c}$ receptors than those of the prior art, synthesized indole carboxylic acid bispyridyl carboxamide derivatives, and identified that the derivatives have high affinity and selectivity for $5\text{-HT}_{2c}$ receptors, thereby leading to completion of the present invention.

DISCLOSURE

Technical Problem

One object of the present invention is to provide an indole carboxylic acid bispyridyl carboxamide derivative or a pharmaceutically acceptable salt thereof.

Another object of the present invention is to provide a method of preparing an indole carboxylic acid bispyridyl carboxamide derivative or a pharmaceutically acceptable salt thereof.

Still another object of the present invention is to provide a 5-$HT_{2c}$ receptor antagonist containing an indole carboxylic acid bispyridyl carboxamide derivative or a pharmaceutically acceptable salt thereof as an active ingredient.

Even another object of the present invention is to provide a composition for prevention or treatment of obesity, containing an indole carboxylic acid bispyridyl, carboxamide derivative or a pharmaceutically acceptable salt thereof as an active ingredient.

Yet another object of the present invention is to provide a composition for prevention or treatment of urinary disorders, containing an indole carboxylic acid bispyridyl carboxamide derivative or a pharmaceutically acceptable salt thereof as an active ingredient.

Further another object of the present invention is to provide a composition for prevention or treatment of central nervous system (CNS) disorders, containing an indole carboxylic acid bispyridyl carboxamide derivative or a pharmaceutically acceptable salt thereof as an active ingredient.

Still further another object of the present invention is to provide a food composition for prevention or improvement of obesity, containing an indole carboxylic acid bispyridyl carboxamide derivative or a pharmaceutically acceptable salt thereof as an active ingredient.

Another object of the present invention is to provide a method for treating a disease in a mammal comprising administering a therapeutically effective amount of an indole carboxylic acid bispyridyl carboxamide derivative or a pharmaceutically acceptable salt thereof to the mammal in need thereof.

Also, another object of the present invention is to provide a use of an indole carboxylic acid bispyridyl carboxamide derivative or a pharmaceutically acceptable salt thereof in the manufacture of a medicament for preventing or treating disease.

Technical Solution

In order to achieve the objects, the present invention provides an indole carboxylic acid bispyridyl carboxamide derivative or a pharmaceutically acceptable salt thereof.

The present invention also provides a method of preparing an indole carboxylic acid bispyridyl carboxamide derivative or a pharmaceutically acceptable salt thereof.

Furthermore, the present invention provides a 5-$HT_{2c}$ receptor antagonist containing an indole carboxylic acid bispyridyl carboxamide derivative or a pharmaceutically acceptable salt thereof as an active ingredient.

The present invention also provides a composition for prevention or treatment of obesity, containing an indole carboxylic acid bispyridyl carboxamide derivative or a pharmaceutically acceptable salt thereof as an active ingredient.

Furthermore, the present invention provides a composition for prevention or treatment of urinary disorders, containing an indole carboxylic acid bispyridyl carboxamide derivative or a pharmaceutically acceptable salt thereof as an active ingredient.

The present invention also provides a composition for prevention or treatment of central nervous system (CNS) disorders, containing an indole carboxylic acid bispyridyl carboxamide derivative or a pharmaceutically acceptable salt thereof as an active ingredient.

Furthermore, the present invention provides a food composition for prevention or improvement of obesity, containing an indole carboxylic acid bispyridyl carboxamide derivative or a pharmaceutically acceptable salt thereof as an active ingredient.

In addition, the present invention provides a method for treating a disease selected from a group consisting of obesity, CNS disorders, and urinary disorders in a mammal, comprising administering a therapeutically effective amount of an indole carboxylic acid bispyridyl carboxamide derivative or a pharmaceutically acceptable salt thereof, to a mammal in need thereof.

Also, the present invention provides a use of an indole carboxylic acid bispyridyl carboxamide derivative or a pharmaceutically acceptable salt thereof in a manufacture of a medicament for treating or preventing a disease selected from a group consisting of obesity, CNS disorders, and urinary disorders.

Advantageous Effects

Because indole carboxylic acid bispyridyl carboxamide derivatives according to the present invention have high affinity for 5-$HT_{2c}$ receptors and act selectively on 5-$HT_{2c}$ receptors only, the derivatives rarely have adverse effects caused by other receptors and effectively inhibit serotonin activity. The derivatives may be also useful for treatment or prevention of obesity, urinary disorders such as urinary incontinence, CNS disorders such as depression and anxiety, and the like.

DESCRIPTION OF DRAWINGS

The above and other objects, features and other advantages of the present invention will be more clearly understood from the following detailed description taken in conjunction with the accompanying drawings, in which:

FIG. 1 is a graph illustrating inhibition rates of activity of G protein bound to a 5-$HT_{2c}$ receptor at different concentrations in one Example of the present invention.

BEST MODE

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides an indole carboxylic acid bispyridyl carboxamide derivatives represented by following Formula (1), or a pharmaceutically acceptable salt thereof.

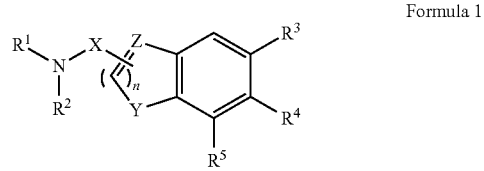

Formula 1 wherein R¹ is

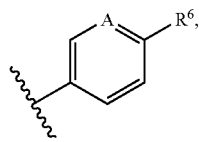

A is C or N, R⁶ is H,

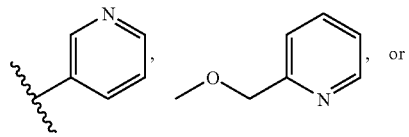

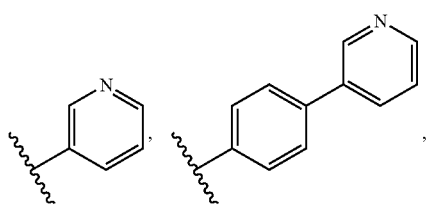

A¹ to A⁵ are independently or selectively C or N, R⁷ to R¹¹ are independently or selectively H, a $C_1$ to $C_5$ linear or branched alkyl group, a $C_1$ to $C_5$ alkoxy group, or halogen, R² is H or a $C_1$ to $C_5$ linear or branched alkyl group, R³ to R⁵ are independently or selectively H, a $C_1$ to $C_5$ alkyl group, a $C_1$ to $C_5$ alkoxy group, or halogen, X is $CH_2$, C=O, C=S, or $SO_2$, Y is O, S, NH, or N—$CH_3$, Z is C or N, and n is 1 or 2.

Preferably, R¹ is

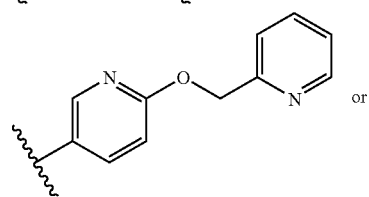

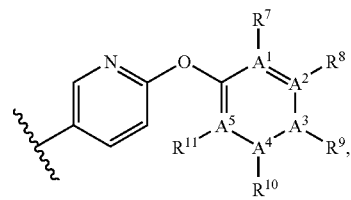

A¹ to A⁵ are independently or selectively C or N, R⁷ to R¹¹ are independently or selectively H, a methyl group, an ethyl group, a propyl group, an isopropyl group, a methoxy group, an ethoxy group, a propoxy group, fluorine, chlorine, bromine, or iodine, R² is H or a $C_1$ to $C_5$ linear or branched alkyl group, R³ to R⁵ are independently or selectively H, a methyl group, an ethyl group, a methoxy group, an ethoxy group, fluorine, chlorine, bromine, or iodine, X is $CH_2$, C=O, C=S, or $SO_2$, Y is O, S, NH, or N—$CH_3$, Z is C or N, and n is 1 or 2.

More preferably, R¹ is selected from the group consisting of

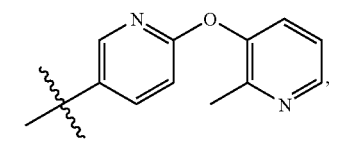

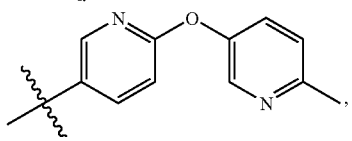

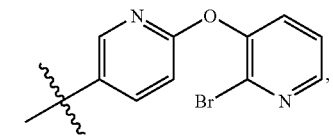

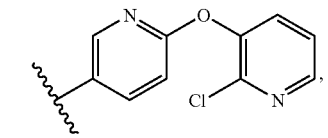

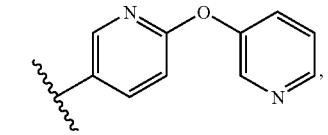

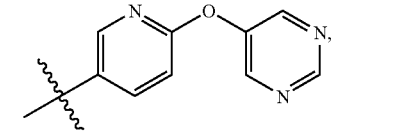

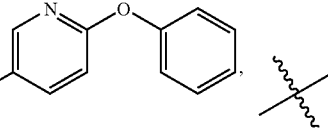

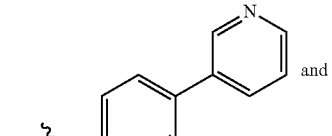

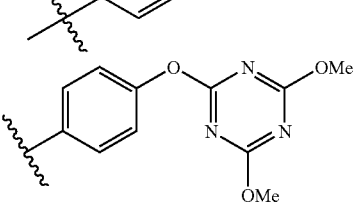

R² is H, a methyl group, or an ethyl group,

R³ is H, a methyl group, a methoxy group, or iodine, $R^4$ or $R^5$ is H or a methyl group,
X is $CH_2$, C=O, C=S, or $SO_2$,
Y is O, S, NH or N—$CH_3$,
Z is C or N, and
n is 1 or 2.

Indole carboxylic acid bispyridyl carboxamide derivatives represented by Formula (1) are exemplified in more detail in the followings.
(1) benzofuran-3-sulfonic acid[6-(2-methyl-pyridine-3-yloxy)-pyridine-3-yl]-amide;
(2) benzo[b]thiophene-3-sulfonic acid[6-(2-methyl-pyridine-3-yloxy)-pyridine-3-yl]-amide;
(3) benzofuran-3-carboxylic acid[6-(2-methyl-pyridine-3-yloxy)-pyridine-3-yl]-amide;
(4) benzo[b]thiophene-3-carboxylic acid[6-(2-methyl-pyridine-3-yloxy)-pyridine-3-yl]-amide;
(5) 1H-indole-2-carboxylic acid[6-(2-methyl-pyridine-3-yloxy)-pyridine-3-yl]-amide;
(6) 1H-indole-3-carboxylic acid[6-(2-methyl-pyridine-3-yloxy)-pyridine-3-yl]-amide;
(7) 1H-benzoimidazole-2-carboxylic acid[6-(2-methyl-pyridine-3-yloxy)-pyridine-3-yl]-amide;
(8) naphthalene-2-carboxylic acid[6-(2-methyl-pyridine-3-yloxy)-pyridine-3-yl]-amide;
(9) (1H-indole-3-ylmethyl)-[6-(2-methyl-pyridine-3-yloxy)-pyridine-3-yl]-amine;
(10) 1H-indole-3-carboxylic acid[6-(2-methyl-pyridine-3-yloxy)-pyridine-3-yl]-amide;
(11) 1-methyl-1H-indole-3-carboxylic acid[6-(2-methyl-pyridine-3-yloxy)-pyridine-3-yl]-amide;
(12) 1H-indole-3-carboxylic acid methyl-[6-(2-methyl-pyridine-3-yloxy)-pyridine-3-yl]-amide;
(13) 1-methyl-1H-indole-3-carboxylic acid methyl-[6-(2-methyl-pyridine-3-yloxy)-pyridine-3-yl]-amide;
(14) 5-methyl-1H-indole-3-carboxylic acid[6-(2-methyl-pyridine-3-yloxy)-pyridine-3-yl]-amide;
(15) 5-methoxy-1H-indole-3-carboxylic acid[6-(2-methyl-pyridine-3-yloxy)-pyridine-3-yl]-amide;
(16) 6-methyl-1H-indole-3-carboxylic acid[6-(2-methyl-pyridine-3-yloxy)-pyridine-3-yl]-amide;
(17) 7-methyl-1H-indole-3-carboxylic acid[6-(2-methyl-pyridine-3-yloxy)-pyridine-3-yl]-amide;
(18) 5-iodo-1H-indole-3-carboxylic acid[6-(2-methyl-pyridine-3-yloxy)-pyridine-3-yl]-amide;
(19) 1H-indole-3-carboxylic acid[6-(pyrimidine-5-yloxy)-pyridine-3-yl]-amide;
(20) 1H-indole-3-carboxylic acid[6-(pyridine-2-ylmethoxy)-pyridine-3-yl]-amide;
(21) 1H-indole-3-carboxylic acid[6-(6-methyl-pyridine-3-yloxy)-pyridine-3-yl]-amide;
(22) 1H-indole-3-carboxylic acid[6-(2-chloro-pyridine-3-yloxy)-pyridine-3-yl]-amide;
(23) 1H-indole-3-carboxylic acid[6-(2-bromo-pyridine-3-yloxy)-pyridine-3-yl]-amide;
(24) 1H-indole-3-carboxylic acid[6-(pyridine-3-yloxy)-pyridine-3-yl]-amide;
(25) 1H-indole-3-carboxylic acid(6-phenoxy-pyridine-3-yl)-amide;
(26) 1H-indole-3-carboxylic acid pyridine-3-ylamide;
(27) 1H-indole-3-carboxylic acid(4-pyridine-3-yl-phenyl)-amide;
(28) 6-methyl-1H-indole-3-carboxylic acid[6-(2-chloro-pyridine-3-yloxy)-pyridine-3-yl]-amide; and
(29) 1H-indole-3-carboxylic acid[4-(4,6-dimethoxy-[1,3,5]triazine-2-yloxy)-phenyl]-amide.

The derivatives of Formula (1) of the present invention may be used in the form of pharmaceutically acceptable salts, and as the salts, acid addition salts formed with pharmaceutically acceptable free acids are useful. Acid addition salts are obtained from inorganic acids, such as hydrochloric, nitric, phosphoric, sulfuric, hydrobromic, hydroiodic, nitrous or phosphorous as well as from nontoxic organic acids such as aliphatic mono- and di-carboxylates, phenyl-substituted alkanoates, hydroxy alkanoates, aromatic acids, aliphatic and aromatic sulfonic acids. These pharmaceutically nontoxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, -hydroxybutyrate, glycollate, malate, tartrate, methanesulfonate, propanesulfonate, naphthalene-1-sulfonate, naphthalene-2-sulfonate or mandelate.

According to the present invention, the acid addition salts may be prepared through conventional methods. For example, acid addition salt can be prepared by dissolving a derivative of Formula (1) in an excessive amount of an acid aqueous solution, and precipitating the salt in a water-miscible organic solvent, such as methanol, ethanol, acetone or acetonitrile.

Acid addition salt may be also prepared by heating a mixture including the same amount of the derivative of Formula (1) and an acid in water or alcohol, and then evaporating and drying the mixture or performing suction filtration onto the precipitated salt.

Further, a pharmaceutically acceptable metal salt may be produced using a base. An alkali metal salt or an alkaline earth metal salt may be obtained for example, by dissolving a compound in an excessive amount of alkali metal hydroxide or alkaline earth metal hydroxide solution, filtering the undissolved salt, and then evaporating and drying the filtrate. In respects to metal salts, sodium, potassium, or calcium salt is pharmaceutically preferable, and the corresponding silver salt is obtained by reacting an alkali metal salt or alkaline earth metal salt with a suitable silver salt (e.g., silver nitrate).

The present invention includes not only indole carboxylic acid bispyridyl carboxamide derivatives represented by above Formula (1) and pharmaceutically acceptable salts thereof, but also all the possible solvates and hydrates which may be formed from these.

The present invention also provides a method of preparing a new indole bispyridyl carboxamide derivative represented by following Reaction Formula 1.

Hereinafter, this will be specifically described.

[Reaction Formula 1]

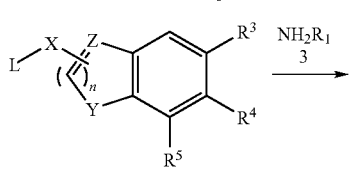

-continued

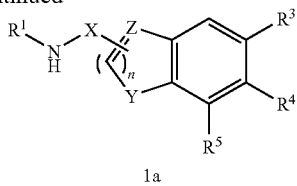

1a where $R^1$ to $R^5$, n, X, Y, and Z are as defined in Formula (1), L is a leaving group that may be easily displaced by an amine, and Formula (1a) is included in Formula (1).

In the preparation method according to the present invention, a substituted heteroaryl derivative of Reaction Formula 2 may include a heteroaryl carboxylic acid derivative, a heteroarylsulfonyl derivative, and the like.

The substituted heteroaryl derivative (2) may be easily substituted when reacted with an amine, due to a leaving group (L) that may be easily displaced. These leaving groups include halide, hydroxyl group, mesylate group, tosylate group, and the like.

The substituted heteroaryl derivative may be easily prepared from a heteroaryl compound substituted by conventionally known methods. For example, a heteroaryl carboxylic derivative may be prepared by a method represented as Reaction Formula 2.

[Reaction Formula 2]

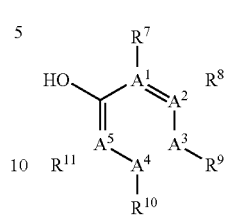

wherein $R^3$ to $R^5$ are as defined in Formula (1), and Formula (2a) is included in Reaction Formula 2.

Specifically, the substituted heteroaryl derivative may be prepared by reacting a suitably substituted indole (4) with a trifluoroacetate anhydride in DMF and producing an indole-3-trifluoroacetate (5) (Step a), and then adding NaOH aqueous solution thereto, hydrolyzing the mixture, and reducing a CF3 group into an OH group (Step b).

In a preparation method according to the present invention, bisarylester amine and the like may be used as an amine compound of Reaction Formula 3, and for example bipyridylester amine may be included.

The bisarylester amine may be easily prepared from a heteroaryl compound substituted by a conventionally known method, and for example bipyridylester amine may be prepared by a method represented as Reaction Formula 3.

[Reaction Formula 3]

wherein A1 to A5 and R7 to R11 are as defined in Formula (1), and Formula (3a) is included in Reaction Formula 3.

Specifically, bisarylester amine (3a) may be prepared by reacting a hydroxypyridine compound with NaH and 2-chloro-5-nitropyridine (7), and then reacting the produced nitropyrimidine with $SnCl_2$ in ethanol and reducing the mixture.

In a preparation method of above Reaction Formula 1 according to the present invention, the heteroaryl derivative (2) may be reacted with an equivalent amine compound under suitable reaction conditions according to the kind of the derivative.

1) When the heteroaryl derivative (2) is a heteroaryl carboxylic acid derivative, a compound of Formula (1) may be prepared by reacting the derivative with the amine compound (3) in a suitable reaction solvent in the presence of a condensing agent and a base at room temperature to the boiling temperature of the solvent.

2) When the heteroaryl derivative (2) is a heteroarylsulfonyl derivative, a compound of Formula (1) may be prepared by reacting the derivative with the amine compound (3) in a suitable reaction solvent in the presence of a base at room temperature.

Available reaction solvents may include ethers such as tetrahydrofuran (THF), 1,4-dioxane, and the like; aromatic hydrocarbons such as benzene, toluene, and the like; halogenated hydrocarbons such as dichloromethane, chloroform, and the like; and acetonitrile, dimethylformamide (DMF) or mixtures thereof.

Available condensing agents may include N,N-carbonyldiimidazole (CDI), dicyclohexylcarbodiimide (DCC), diisopropylcarbodiimide (DIPC), 1-ethyl-3-(3-dimethylaminopropyl)carbodiimide (EDC), O-(benzotriazol-1-yl)-N,N,N', N'-tetramethyluronium hexafluorophosphate (HBTU), and the like.

Available bases may include pyridine, diisopropylethylamine, triethylamine, 1,8-diazabicyclo-[5.4.0]undec-7-ene (DBU), and the like.

As an amine in a compound of Formula (1a) prepared by the above method is described in following Reaction Formula 4, an alkyl group (R2) may be additionally introduced by a nucleophilic substitution reaction.

[Reaction Formula 4]

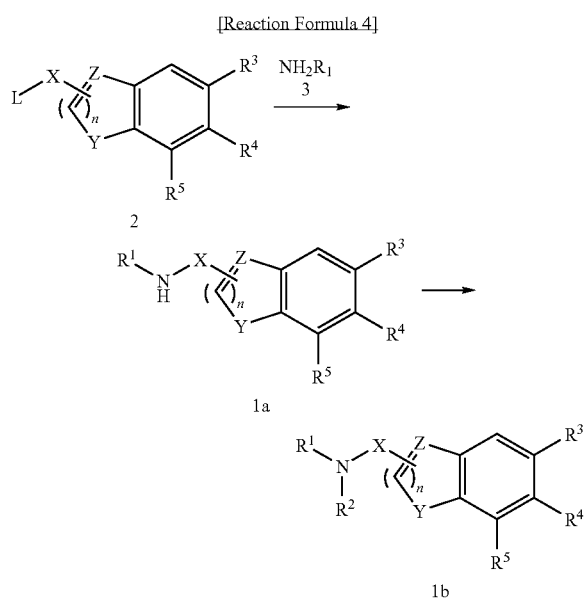

wherein $R^1$ to $R^5$, n, X, Y, and Z are as defined in Formula (1), L is a leaving group that may be easily displaced by an amine, and Formula (1a) and Formula (1b) are included in Formula (1).

Furthermore, the present invention provides a 5-HT2c receptor antagonist containing derivatives of Formula (1) or pharmaceutically acceptable salts thereof as an active ingredient.

The present invention also provides a composition for prevention or treatment of obesity, containing a derivative of Formula (1) or a pharmaceutically acceptable salt thereof as an active ingredient.

The present invention also provides a composition of prevention or treatment of urinary disorders, containing a derivative of Formula (1) or a pharmaceutically acceptable salt thereof as an active ingredient.

The present invention also provides a composition of prevention or treatment of CNS disorders, containing a derivative of Formula (1) 1 or a pharmaceutically acceptable salt thereof as an active ingredient.

$5\text{-HT}_{2c}$ is transcribed and expressed in hypothalamic structure associated with appetite regulation, and it has been demonstrated through various researches that the $5\text{-HT}_{2c}$ receptor is involved in obesity treatment. For example, the $5\text{-HT}_{2c}$ receptor agonist m-chlorophenylpiperazine (mCPP), which has some preference for the $5\text{-HT}_{2c}$ receptor, reduces food intake in mice that express the normal $5\text{-HT}_{2c}$ receptor while the compound lacks activity in mice expressing the mutated inactive form of the $5\text{-HT}_{2c}$ receptor (Nature (1995), 374, 542-546). In a recent clinical study, a sustained reduction in body weight was obtained after 2 weeks of treatment with mCPP in obese subjects (Psychopharmacology (1997), 133, 309-312).

In addition, the $5\text{-HT}_{2c}$ receptor has been known to be involved in CNS disorders such as depression and anxiety (IDrugs (1999), 2, 109-120) and urinary disorders such as urinary incontinence (IDrugs (1998), 1, 456-470). Compounds which have a selective effect on the $5\text{-HT}_{2c}$ receptor may therefore have a therapeutic potential in the treatment of disorders like those mentioned above.

In an experiment of binding to 5-HT2c receptors, derivatives represented by above Formula (1) according to the present invention showed activities equivalent to or better than those of conventional 5-HT2c receptors (See Table 2), and in a receptor selectivity experiment, similar receptors (5-HT1a, 5-HT2a, 5-HT6, 5-HT7, D2, D3, and D4) other than 5-TH2c receptors showed almost no activity as IC50 values of 1000 or more. From the results, it may be known that 5-HT2c receptors have excellent selectivity (See Table 3).

Thus, a composition containing derivatives represented by above Formula (1) or pharmaceutically acceptable salts thereof as an active ingredient selectively inhibits serotonin activity for 5-HT2c receptors and may be useful for treatment or prevention of obesity; urinary disorders such as urinary incontinence, premature ejaculation, erectile dysfunction, and prostatic hyperplasia; CNS disorders such as depression, anxiety, concern, panic disorder, epilepsy, obsessive-compulsive disorder, migraine, sleep disorder, withdrawal from drug abuse, Alzheimer's disease, and schizophrenia, associated with 5-HT2c receptors.

When a composition of the present invention is used as a medicine, a pharmaceutical composition containing derivatives represented by Formula (1) or pharmaceutically acceptable salts thereof as an active ingredient may be prepared and administered in various oral or parenteral dosage forms as follows, but is not limited thereto.

Formulations for oral administration include, for example, tablets, pills, hard/soft capsules, liquid solutions, suspensions, emulsions, syrups, granules, elixirs, and the like. These formulations may contain, in addition to the active ingredient, diluents (e.g., lactose, dextrose, sucrose, mannitol, sorbitol, cellulose and/or glycerin) and lubricants (e.g., silica, talc, stearic acid or salts thereof, such as magnesium or calcium stearate, and/or polyethylene glycol). Tablets may also contain binding agents such as magnesium aluminum silicate, starch paste, gelatin, methyl cellulose, sodium carboxymethylcellulose and/or polyvinylpyrrolidone, and, if desired, disintegrators, e.g., starches, agar, alginic acid or sodium salts thereof, and/or effervescent mixtures, and/or adsorption agents, colorants, flavoring agents and sweeteners.

A pharmaceutical composition containing derivatives represented by Formula (1) as an active ingredient may be parenterally administered, and parenteral administration may be by subcutaneous, intravenous, intramuscular or intrasternal injection.

In order to make a composition suitable for parenteral administration, piperidine derivatives of Formula (1) or pharmaceutically acceptable salts thereof ought to be mixed with stabilizers or buffers in water to make solutions or suspensions, which may be formulated in a unit dosage form of ampoules or vials. The composition may be sterilized and/or contain adjuvants, such as preserving, stabilizing, wetting or emulsifying agents, salts for regulating the osmotic pressure and/or buffers. In addition, the composition may also contain other therapeutically useful substances. The composition may be prepared according to conventional mixing, granulating or coating methods. Derivatives of Formula (1) as an active ingredient may be administered orally or parenterally to mammals including humans, in an amount of 0.1 to 500 mg/kg (body weight), and preferably 0.5 to 100 mg/kg (body weight), once a day or in fractional doses.

Furthermore, the present invention provides a food composition for prevention or improvement of obesity, including derivatives of Formula (1) and sitologically acceptable supplemental additives.

The food composition of the present invention may be added to health foods for prevention or improvement of obesity. When a compound of Formula (1) of the present invention is used as an additive, the compound may be added as such or jointly used with other foods or food ingredients and suitably used in a usual manner. A blending amount of an active ingredient may be appropriately determined according to the purpose of use (prevention, health or therapeutic treatment). In general, when food or beverage is manufactured, the compound of Formula (1) 1 of the present invention is added at a ratio of 1 to 20% by weight of a raw material, and preferably 5 to 10% by weight. However, for health and hygiene or long-term intake for health control, the amount can be less than the above range, but the active ingredient can be used more than the above range because there is no problem in terms of safety issue.

There is no specific limitation in kinds of the food. Examples of foods in which the material may be added include beverages, gums, vitamin complexes, or health supplement food, and all kinds of health food in general meaning are included.

Health beverage compositions of the present invention may contain various flavors or natural carbohydrate as additional ingredient just like general beverage. The natural carbohydrate include monosaccharide such as, glucose and fructose, disaccharide such as maltose and sucrose, polysaccharide such as dextrin and cyclodextrin, and sugar alcohol such as xylitol, sorbitol, erythritol, and the like. For sweetener, natural sweeteners such as thaumatin and stevia extract, or synthetic sweeteners such as saccharin and aspartame may be used. In general, the content of the natural carbohydrate is approximately 0.01 to approximately 0.04 g/100 ml of the composition of the present invention, preferably approximately 0.02 to approximately 0.03 g/100 ml.

In addition, the composition of the present invention may contain various nutrients, vitamins, an electrolyte, flavors, colorants, pectic acid and salt thereof, organic acid, protective colloidal thickener, pH control agent, stabilizer, preservative, glycerin, alcohol, carbonated agent used in carbonated drinks, and the like. Further, the composition of the present invention may contain natural fruit juice and pulp for preparing fruit juice beverage and vegetable beverage. Such ingredients may be used alone or in combination. The ratio of the additive is not very important, but is generally selected from the range of the weight ratio of 0.01 to 0.1 by 100 weight of the composition of the present invention.

Furthermore, the present invention provides a method for treating a disease, selected form obesity, urinary disorders (such as urinary incontinence, premature ejaculation, erectile dysfunction, and prostatic hyperplasia) and CNS disorders (such as depression, anxiety, concern, panic disorder, epilepsy, obsessive-compulsive disorder, migraine, sleep disorder, withdrawal from drug abuse, Alzheimer's disease, and schizophrenia), associated with 5-HT$_{2c}$ receptors, in a mammal, comprising administering a therapeutically effective amount of an indole carboxylic acid bispyridyl carboxamide derivative or a pharmaceutically acceptable salt thereof, to a mammal in need thereof.

The present invention provides a method for treating a 5-HT$_{2c}$ receptor mediated disease in a mammal, comprising administering therapeutically effective amount of an indole carboxylic acid bispyridyl carboxamide derivative or a pharmaceutically acceptable salt thereof, to a mammal in need thereof.

Also, the present invention provides a use of an indole carboxylic acid bispyridyl carboxamide derivative or a pharmaceutically acceptable salt thereof in a manufacture of a medicament for treating or preventing a disease selected form selected form obesity, urinary disorders (such as urinary incontinence, premature ejaculation, erectile dysfunction, and prostatic hyperplasia) and CNS disorders (such as depression, anxiety, concern, panic disorder, epilepsy, obsessive-compulsive disorder, migraine, sleep disorder, withdrawal from drug abuse, Alzheimer's disease, and schizophrenia), associated with 5-HT$_{2c}$ receptors.

Mode for Invention

Hereinafter, the present invention will be described in more detail with reference to the following examples and experimental examples. However, the following examples and experimental examples are provided for illustrative purposes only, and the scope of the present invention should not be limited thereto in any manner.

PREPARATION EXAMPLE

Example 1

Preparation of benzofuran-3-sulfonic acid[6-(2-methyl-pyridine-3-yloxy)-pyridine-3-yl]-amide

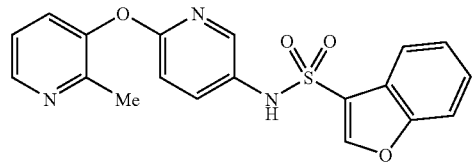

2-methyl-3-hydroxy pyridine (1 g, 9.16 mol) was dissolved in DMF (30 ml) and the solution was stirred with NaH (390 mg, 9.62 mmol) and 2-chloro-5-nitropyridine (1.45 g, 9.16 mmol) at room temperature for 1 hour. And then, the product was filtered and washed, dried under reduced pressures to yield a solid product (2.12 g, 100%). The solid product (2.12 g) was added to a mixed solution of ethanol (62 ml) and hydrochloric acid (16 ml). SnCl2 (7.23 g, 32 mmol) was added to the mixture and stirred for 50 min to 1 hour. Subsequently, the product was filtered, washed, and then dried to prepare a bispyridine ester amine compound (1.63 g, 89%).

Benzofuran (2 g, 16.9 mmol) was added to a solution in which sulfonyl chloride (3.88 g, 28.8 mmol) was dissolved in DMF (6.4 ml) at 0° C., and the mixture was stirred at 85° C. for 3 hours. After the reaction was completed, the product was filtered, washed, and dried to prepare benzofuran-3-sulfonylchloride (6 g, 28 mmol).

The bispyridine ester amine compound (70 mg, 0.35 mmol) and benzofuran-3-sulfonylchloride (75 mg, 0.35 mmol) were dissolved in dichloromethane (5 ml), triethylamine (0.07 g, 0.70 mmol) was added to the solution and the mixture was stirred at room temperature for 2 hours. After the reaction was completed, the product was washed and filtered to yield a target compound as a yellow solid (0.03 g, 23%) by chromatography (methanol:dichloromethane=1:20).

Example 2

Preparation of benzo[b]thiophene-3-sulfonic acid[6-(2-methyl-pyridine-3-yloxy)-pyridine-3-yl]-amide

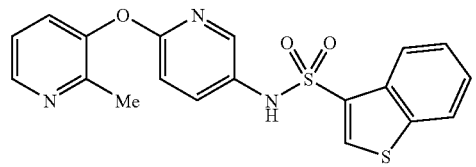

Sulfuric acid (2 ml, 0.037 mmol) was added to thianaphthene (5 g, 0.037 mmol) in anhydrous acetic acid (4.9 g, 0.048 mmol) at 0° C. The mixture was stirred at room temperature for 3 hours, iced water (30 ml) was added and the mixture was washed with diethylether. Potassium 3-thianaphthene sulfonate (6 g, 0.024 mmol) was obtained from recrystalization of crystals produced by treatment of the water layer with a hot saturated solution of potassium chloride (3 g potassium chloride/30 ml, water). The produced salt (2.5 g, 0.01 mmol) was stirred in a solution of PCl5 (2.9 g, 13.96 mmol) at room temperature for 1 hour. Subsequently, the product was filtered, washed, and dried to obtain benzo[b]thiophene-3-sulfonylchloride.

The bispyridine ester amine compound (120 mg, 0.60 mmol) in Example 1 and benzo[b]thiophene-3-sulfonylchloride (75 mg, 0.35 mmol) were dissolved in dichloromethane (5 ml), triethylamine (0.14 g, 0.60 mmol) was added to the solution and the mixture was stirred at room temperature for 2 hours. After the reaction was completed, the product was washed and filtered to yield a target compound as a white solid (0.34 g, 66%) by chromatography (methanol:dichloromethane=1:20).

Example 3

Preparation of benzofuran-3-carboxylic acid[6-(2-methyl-pyridine-3-yloxy)-pyridine-3-yl]-amide

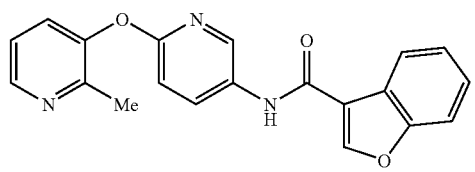

Benzofuran-1,3-dicarboxylic acid (1 g, 4.85 mmol) was heated to 280° C., its boiling temperature, and then was stirred at the temperature for 10 min. The reactant was cooled to room temperature, and then an organic material in acetone was extracted and dried to obtain a yellow solid benzofuran-3-carboxylic acid (100 mg, 0.62 mmol).

The bispyridine ester amine compound (100 mg, 0.50 mmol) in Example 1 and benzofuran-3-carboxylic acid (100 mg, 0.62 mmol) were dissolved in dichloromethane (5 ml), DCC (100 mg, 0.48 mmol) was added to the solution, and the mixture was stirred at 80° C. for 8 hours. After the reaction was completed, the product was washed and filtered to yield a target compound as a white solid (9.3 mg, 10%) by chromatography (methanol:dichloromethane=1:30).

Example 4

Preparation of benzo[b]thiophene-3-carboxylic acid [6-(2-methyl-pyridine-3-yloxy)-pyridine-3-yl]-amide

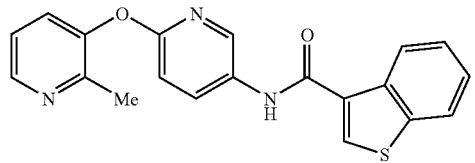

3-bromothianaphthene (1.63 g, 7.65 mmol) was dissolved in anhydrous ether (30 ml) and n-BuLi (2.5 M, 3.5 ml, 8.65 mmol) was added to the solution at −78° C. The mixture was stirred at −78° C. for 10 min, and then the reaction solution was slowly added to an excessive amount of dry ice dissolved in anhydrous ether (140) under nitrogen conditions. The mixture was heated to room temperature for 1 hour, and then stirred at room temperature for another 2 hours. After the reaction was completed, the product was washed, filtered, and dried to obtain benzo[b]thiophene-3-carboxylic acid (805 mg, 4.51 mmol).

The bispyridine ester amine compound (68 mg, 0.34 mmol) in Example 1 and benzo[b]thiophene-3-carboxylic acid (60 mg, 0.34 mmol) were dissolved in DMF (5 ml), HBTU (128 mg, 0.34 mmol) and triethylamine (0.14 ml, 1.01 mmol) were added to the solution, and the mixture was stirred at room temperature for 24 hours. After the reaction was completed, the product was washed and filtered to yield a target compound as a white solid (70 mg, 58%) by chromatography (methanol:dichloromethane=1:30).

Example 5

Preparation of 1H-indole-2-carboxylic acid[6-(2-methyl-pyridine-3-yloxy)-pyridine-3-yl]-amide

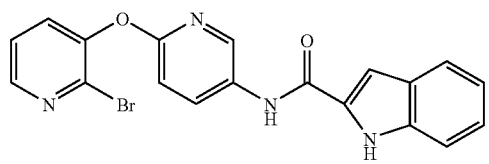

The bispyridine ester amine compound (120 mg, 0.62 mmol) in Example 1 and 1H-indole-2-carboxylic acid (100 ml, 0.62 mmol) were dissolved in DMF (5 ml), HBTU (240 mg, 0.62 mmol) was added to the solution, and the mixture was stirred at 80° C. for 8 hours. After the reaction was completed, the product was washed and filtered to yield a target compound as a brown solid (30 mg, 14%) by chromatography (methanol:dichloromethane=1:30).

Example 6

Preparation of 1H-indole-3-carboxylic acid[6-(2-methyl-pyridine-3-yloxy)-pyridine-3-yl]-amide

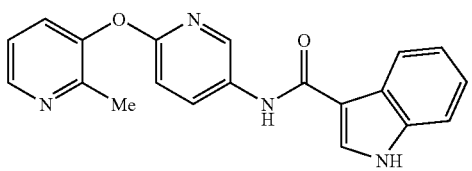

The bispyridine ester amine compound (100 mg, 0.50 mmol) in Example 1 and indole-3-carboxylic acid (76 mg, 0.47 mmol) were dissolved in DMF (3 ml), DCC (113 mg, 0.55 mmol) was added to the solution, and the mixture was stirred at 80° C. for 3 hours. After the reaction was completed, the product was washed and filtered to yield a target compound as a yellowish solid (80 mg, 47%) by chromatography (methanol:dichloromethane=1:20).

product was washed and filtered to yield a target compound as a brown solid (16 mg, 10%) by chromatography (methanol:dichloromethane=1:30).

Example 7

Preparation of 1H-benzoimidazole-2-carboxylic acid [6-(2-methyl-pyridine-3-yloxy)-pyridine-3-yl]-amide

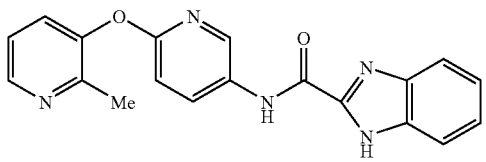

1,2-phenylenediamine (1 g, 9.25 mmol) was dissolved in acetic acid (30 ml), methyltrichloroacetimidate (1.26 ml, 10.18 mmol) was added to the solution at 0° C. and then the mixture was stirred at room temperature. After the reaction was completed, the product was washed, filtered, and dried to obtain 2-trichloromethyl-1H-benzoimidazole. 2-trichloromethyl-1H-benzoimidazole thus obtained was added to 2 N aqueous sodium hydroxide solution (50 ml) at 0° C. and the mixture was stirred at the temperature for 2 hours. The mixture was acidified with 2 N aqueous hydrochloric, acid (pH=3) and the resulting crystals were washed and filtered to obtain 1H-benzoimidazole-2-carboxylic acid (1.2 g, 2-step yield: 80%).

The bispyridine ester amine compound (168 mg, 0.83 mmol) in Example 1 and benzoimidazole-2-carboxylic acid (190 mg, 1.17 mmol) were dissolved in DMF (5 ml), HBTU (402 mg, 1.25 mmol) and triethylamine (0.58 ml, 4.17 mmol) were added to the solution, and the mixture was stirred at room temperature for 24 hours. After the reaction was completed, the product was washed and filtered to yield a target compound as a white solid (247 mg, 86%) by chromatography (methanol:dichloromethane=1:30).

Example 8

Preparation of naphthalene-2-carboxylic acid[6-(2-methyl-pyridine-3-yloxy)-pyridine-3-yl]-amide

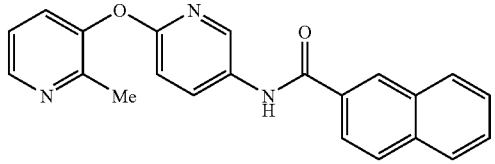

The bispyridine ester amine compound (90 mg, 0.46 mmol) in Example 1 and 2-naphthoic acid (80 mg, 0.46 mmol) were dissolved in DMF (5 ml), DCC (90 mg, 0.46 mmol) was added to the solution, and the mixture was stirred at 60° C. for 8 hours. After the reaction was completed, the Example 9

Preparation of (1H-indole-3-ylmethyl)-[6-(2-methyl-pyridine-3-yloxy)-pyridine-3-yl]-amine

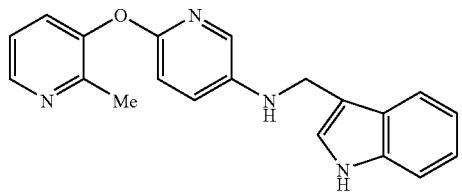

The bispyridine ester amine compound (100 mg, 0.50 mmol) in Example 1 and indole-3-carboxaldehyde (66 mg, 0.45 mmol) were dissolved in 1,2-dichloroethane (3 ml), sodium triacetoxyborohydride (142 mg, 0.64 mmol) and acetic acid (0.03 ml, 0.45 mmol) were added to the solution, and the mixture was stirred at room temperature for 8 hours. After the reaction was completed, the product was washed and filtered to yield a target compound as a colorless liquid (29 mg, 19%) by chromatography (methanol:dichloromethane=2:30)

Example 10

Preparation of 1H-indole-3-carboxylic acid[6-(2-methyl-pyridine-3-yloxy)-pyridine-3-yl]-amide

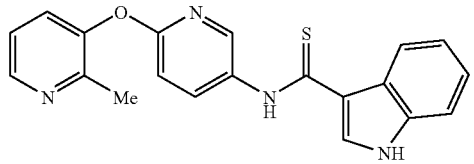

The 1H-indole-3-carboxylic acid[6-(2-methyl-pyridine-3-yloxy)-pyridine-3-yl]-amide (0.1 g, 0.29 mmol) in Example 6 was dissolved in toluene (3 ml), and Lawesson s reagent (0.07 g, 0.17 mmol) was added to the solution. The reaction solution was heated to 80° C. for 14 hours, and then the product was washed and filtered to yield a target compound as a white solid (93 mg, 89%) by chromatography (methanol:dichloromethane=1:30).

Example 11

Preparation of 1-methyl-1H-indole-3-carboxylid acid[6-(2-methyl-pyridine-3-yloxy)-pyridine-3-yl]-amide

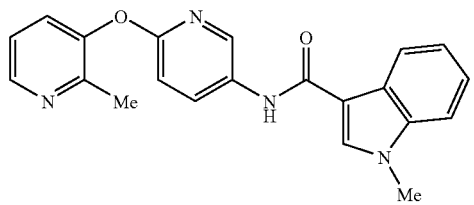

The 1H-indole-3-carboxylic acid[6-(2-methyl-pyridine-3-yloxy)-pyridine-3-yl]-amide (0.1 g, 0.29 mmol) in Example 6 was dissolved in THF (10 ml), and NaH (6.9 mg, 0.29 mmol) and methyl iodide (0.04 g, 0.29 mmol) were added to the solution. The reaction solution was stirred at room temperature for 8 hours, and then the product was washed and filtered to yield a target compound as a white solid (94 mg, 90%) by chromatography (methanol:dichloromethane=1:30).

Example 12

Preparation of 1H-indole-3-carboxylic acid methyl-[6-(2-methyl-pyridine-3-yloxy)-pyridine-3-yl]-amide

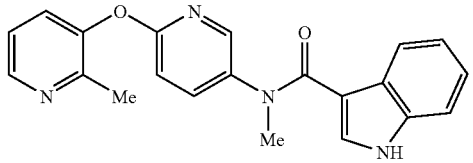

The 1H-indole-3-carboxylic acid[6-(2-methyl-pyridine-3-yloxy)-pyridine-3-yl]-amide (0.2 g, 0.58 mmol) in Example 6 was dissolved in dichloromethane (10 ml), and Boc₂O (0.15 g, 0.7 mmol) and triethylamine (0.12 g, 1.16 mmol) were added to the solution. The reaction solution was stirred at room temperature for 2 hours, and then the product was washed, filtered, and dried to obtain tert-butyl-3-(6-(2-methylpyridine-3-yloxy)pyridine-3-ylcarbamoyl)-1H-indole-1-carboxylate (0.27 g, 0.52 mmol). The tert-butyl-3-(6-(2-methylpyridine-3-yloxy)pyridine-3-ylcarbamoyl)-1H-indole-1-carboxylate (0.27 g, 0.52 mmol) was dissolved in THF (10 ml), and NaH (21 mg, 0.54 mmol) and methyl iodide (0.95 g, 0.67 mmol) were added to the solution. The reaction solution was stirred at room temperature for 5 hours, and then the product was washed and filtered to yield tert-butyl-3-(methyl(6-(2-methylpyridine-3-yloxy)pyridine-3-yl)carbamoyl)-1H-indole-1-carboxylate (40 mg, 0.087 mmol) by chromatography (methanol:dichloromethane=1:20).

The tert-butyl-3-(methyl(6-(2-methylpyridine-3-yloxy)pyridine-3-yl)carbamoyl)-1H-indole-1-carboxylate (40 mg, 0.087 mmol) was added to a mixed solution of dichloromethane (1 ml) and TFA (1 ml), and the mixture was stirred at room temperature for 1 hour. Subsequently, the product was filtered, washed, and dried to yield a target compound as a white solid (28 mg, 90%)

Example 13

Preparation of 1-methyl-1H-indole-3-carboxylic acid methyl-[6-(2-methyl-pyridine-3-yloxy)-pyridine-3-yl]-amide

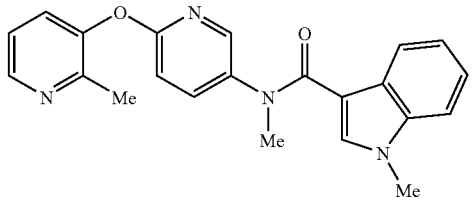

The tert-butyl-3-(methyl(6-(2-methylpyridine-3-yloxy)pyridine-3-yl)carbamoyl)-1H-indole-1-carboxylate (40 mg, 0.087 mmol) in Example 12 was dissolved in THF (10 ml), and NaH (21 mg, 0.54 mmol) and methyl iodide (0.95 g, 0.67 mmol) were added to the solution. The reaction solution was stirred at room temperature for 5 hours, and then the product was washed and filtered to yield a target compound as a brown solid (20 mg, 12%) by chromatography (methanol:dichloromethane=1:20).

Example 14

Preparation of 5-methyl-1H-indole-3-carboxylic acid [6-(2-methyl-pyridine-3-yloxy)-pyridine-3-yl]-amide

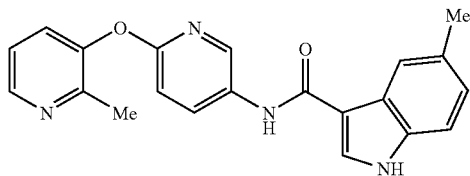

5-methyl indole (1 g, 7.62 mmol) was dissolved in DMF (20 ml), and then trifluoroacetic anhydride (2.1 ml, 15.24 mmol) was added to the solution, and the mixture was stirred at room temperature for 2 hours. Subsequently, the product was filtered, washed, and dried to prepare 2,2,2-trifluoro-1-(5-methyl-1H-indole-3-yl)ethanone (1.7 g, 7.47 mmol).

The 2,2,2-trifluoro-1-(5-methyl-1H-indole-3-yl)ethanone (0.25 g, 1.10 mmol) was dissolved in 20% aqueous sodium hydroxide solution (5 ml) and the mixture was stirred at 50° C. for 8 hours. Subsequently, the product was filtered, washed, and dried to prepare 5-methyl-1H-indole-3-carboxylic acid (0.14 g, 0.84 mmol).

The bispyridine ester amine compound (100 mg, 0.50 mmol) in Example 1 and 5-methyl-1H-indole-3-carboxylic acid (100 mg, 0.57 mmol) were dissolved in DMF (3 ml), DCC (100 mg, 0.55 mmol) was added to the solution, and then the mixture was stirred at 80° C. for 8 hours. After the reaction was completed, the product was washed and filtered to yield a target compound as a white solid (90 mg, 44%) by chromatography (methanol:dichloromethane=1:30).

Example 15

Preparation of 5-methoxy-1H-indole-3-carboxylic acid[6-(2-methyl-pyridine-3-yloxy)-pyridine-3-yl]-amide

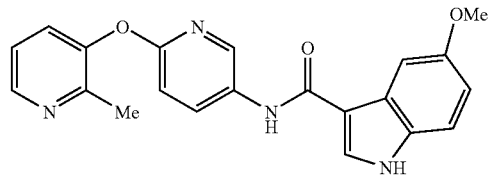

5-methoxy indole (1 g, 6.8 mmol) was dissolved in DMF (30 ml), and then trifluoroacetic anhydride (2.9 g, 13.6 mmol) was added to the solution, and the mixture was stirred at 60° C. for 1 hour. Subsequently, the product was filtered, washed, and dried to prepare 2,2,2-trifluoro-1-(5-methoxy-1H-indole-3-yl)ethanone (1.5 g, 6.19 mmol).

The 2,2,2-trifluoro-1-(5-methoxy-1H-indole-3-yl)ethanone (1 g, 4.13 mmol) was dissolved in 20% aqueous sodium hydroxide solution (15 ml) and the mixture was stirred at 60° C. for 3 hours. Subsequently, the product was filtered, washed, and dried to prepare 5-methoxy-1H-indole-3-carboxylic acid (0.7 g, 3.35 mmol).

The bispyridine ester amine compound (100 mg, 0.50 mmol) in Example 1 and 5-methoxy-1H-indole-3-carboxylic acid (140 mg, 0.75 mmol) were dissolved in DMF (10 ml), DCC (100 mg, 0.55 mmol) was added to the solution, and then the mixture was stirred at 80° C. for 8 hours. After the reaction was completed, the product was washed and filtered to yield a target compound as a colorless liquid (20 mg, 11%) by chromatography (methanol:dichloromethane=1:30).

Example 16

Preparation of 6-methyl-1H-indole-3-carboxylic acid [6-(2-methyl-pyridine-3-yloxy)-pyridine-3-yl]-amide

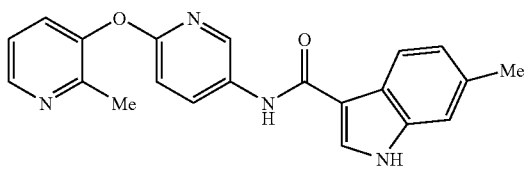

6-methyl indole (0.5 g, 3.81 mmol) was dissolved in DMF (5 ml), and then trifluoroacetic anhydride (1.6 g, 7.62 mmol) was added to the solution, and the mixture was stirred at room temperature for 4 hours. Subsequently, the product was filtered, washed, and dried to prepare 2,2,2-trifluoro-1-(6-methyl-1H-indole-3-yl)ethanone (0.85 g, 3.73 mmol).

The 2,2,2-trifluoro-1-(6-methyl-1H-indole-3-yl)ethanone (0.5 g, 2.20 mmol) was dissolved in 20% aqueous sodium hydroxide solution (5 ml) and the mixture was stirred at 60° C. for 3 hours. Subsequently, the product was filtered, washed, and dried to prepare 6-methyl-1H-indole-3-carboxylic acid (0.3 g, 1.72 mmol).

The bispyridine ester amine compound (100 ml, 0.50 mmol) in Example 1 and 6-methyl-1H-indole-3-carboxylic acid (100 mg, 0.57 mmol) were dissolved in DMF (5 ml), DCC (100 ml, 0.55 mol) was added to the solution, and then the mixture was stirred at 80° C. for 8 hours. After the reaction was completed, the product was washed and filtered to yield a target compound as a white solid (93 mg, 45%) by chromatography (methanol:dichloromethane=1:30).

Example 17

Preparation of 7-methyl-1H-indole-3-carboxylic acid [6-(2-methyl-pyridine-3-yloxy)-pyridine-3-yl]-amide

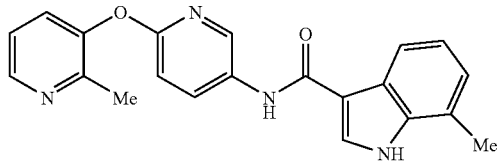

7-methyl indole (0.5 g, 3.81 mmol) was dissolved in DMF (5 ml), and then trifluoroacetic anhydride (1.6 g, 7.62 mmol) was added to the solution, and the mixture was stirred at room temperature for 4 hours. Subsequently, the product was filtered, washed, and dried to prepare 2,2,2-trifluoro-1-(7-methyl-1H-indole-3-yl)ethanone (0.8 g, 3.52 mmol).

The 2,2,2-trifluoro-1-(7-methyl-11H-indole-3-yl)ethanone (0.5 g, 2.20 mmol) was dissolved in 20% aqueous sodium hydroxide solution (5 ml) and the mixture was stirred at 60° C. for 3 hours. Subsequently, the product was filtered, washed, and dried to prepare 7-methyl-1H-indole-3-carboxylic acid (0.3 g, 1.72 mmol).

The bispyridine ester amine compound (200 mg, 0.99 mmol) in Example 1 and 7-methyl-1H-indole-3-carboxylic acid (170 mg, 0.99 mmol) were dissolved in DMF (5 ml), DCC (230 mg, 1.09 mmol) was added to the solution, and then the mixture was stirred at 80° C. for 8 hours. After the reaction was completed, the product was washed and filtered to yield a target compound as a white solid (30 ml, 7%) by chromatography (methanol:dichloromethane=1:30).

Example 18

Preparation of 5-iodo-1H-indole-3-carboxylic acid [6-(2-methyl-pyridine-3-yloxy)-pyridine-3-yl]-amide

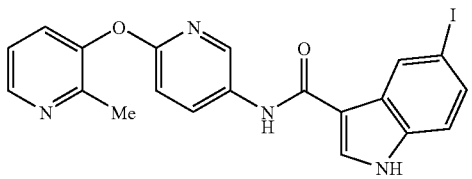

5-iodo indole (1.0 g, 4.11 mmol) was dissolved in DMF (30 ml), and then trifluoroacetic anhydride (1.7 g, 8.22 mmol) was added to the solution, and the mixture was stirred at room temperature for 1 hour. Subsequently, the product was filtered, washed, and dried to prepare 2,2,2-trifluoro-1-(5-iodo-1H-indole-3-yl)ethanone (1.9 g, 2.96 mmol).

The 2,2,2-trifluoro-1-(5-iodo-1H-indole-3-yl)ethanone (0.5 g, 1.47 mmol) was dissolved in 20% aqueous sodium hydroxide solution (5 ml) and the mixture was stirred at 60° C. for 3 hours. Subsequently, the product was filtered, washed, and dried to prepare 5-iodo-1H-indole-3-carboxylic acid (0.35 g, 1.22 mmol).

The bispyridine ester amine compound (100 mg, 0.50 mmol) in Example 1 and 5-iodo-1H-indole-3-carboxylic acid (100 ml, 0.50 mmol) were dissolved in DMF (5 ml), DCC (100 ml, 0.55 mmol) was added to the solution, and then the mixture was stirred at 80° C. for 8 hours. After the reaction was completed, the product was washed and filtered to yield a target compound as a white solid (18 mg, 11%) by chromatography (methanol:dichloromethane=1:30).

Example 19

Preparation of 1H-indole-3-carboxylic acid[6-(pyrimidin-5-yloxy)-pyridine-3-yl]-amide

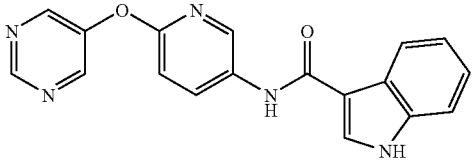

5-bromopyrimidine (5.0 g, 31.4 mmol) and sodium methoxide (1.99 g, 34.9 mmol) were dissolved in MeOH (50 ml), and the mixture was heated in a sealed tube at 150° C. for 24 hours. After the reaction was completed, the product was washed and filtered to prepare 5-methoxy pyrimidine (1.9 g, 2.96 mmol) by chromatography (ethyl acetate:n-hexane=1:1).

NaH (0.91 g, 22.8 mmol) was dissolved in DMF (15 ml), ethanethiol (0.84 ml, 11.4 mmol) was added to the solution, and the mixture was stirred at room temperature for 30 min. 5-methoxy pyrimidine (628 mg, 5.65 mmol) was added to the mixture and stirred at 100° C. for 4 hours. Subsequently, the product was filtered, washed, and dried to prepare pyrimidine-5-ol (681 mg, 5.65 mmol).

Pyrimidine-5-ol (0.39 g, 4.02 mmol) was dissolved in DMF (10 ml), and the solution was stirred with NaH (210 mg, 5.23 mmol) and 2-chloro-5-nitro pyridine (0.64 g, 4.04 mmol) at room temperature for 1 hour. Subsequently, the product was filtered, washed, and dried under reduced pressures to yield a solid product (0.77 g, 87%). The solid product (0.2 g, 0.92 mmol) was added to a mixed solution of ethanol (7 ml) and conc. hydrochloric acid (2 ml), SnCl$_2$ (0.72 g, 3.22 mmol) was added to the mixture, and the resulting solution was stirred at 60° C. for 1 hour. And then the product was filtered, washed, and dried to prepare 6-(pyrimidine-5-yloxy)-pyridine-3-ylamine (0.17 g, 96%).

The 6-(pyrimidine-5-yloxy)-pyridine-3-ylamine (53 mg, 0.28 mmol) and indole-3-carboxylic acid (45 mg, 0.28 mmol) were dissolved in DMF (5 ml), DCC (58 mg, 0.28 mmol) was added to the solution, and then the mixture was stirred at 80° C. for 8 hours. After the reaction was completed, the product was washed and filtered to yield a target compound as a white solid (55 mg, 59%) by chromatography (methanol:dichloromethane=2:30).

Example 20

Preparation of 1H-indole-3-carboxylic acid[6-(pyridine-2-ylmethoxy)-pyridine-3-yl]-amide

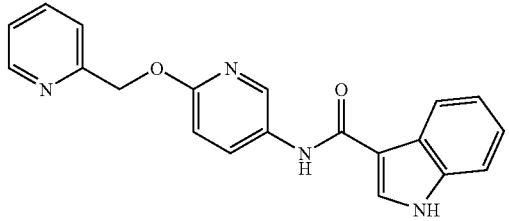

2-pyridinemethanol (2.43 g, 22.3 mmol) was dissolved in DMF (30 ml), and the solution was stirred with NaH (790 mg, 19.8 mmol) and 2-chloro-5-nitro pyridine (3.19 g, 20.1 mmol) at room temperature for 1 hour. Subsequently, the product was filtered, washed, and dried under reduced pressures to yield a solid product (3.47 g, 67%). The solid product (3.72 g, 16.1 nmol) was added to a mixed solution of ethanol (90 ml) and conc. hydrochloric acid (28 ml), SnCl2 (12.7 g, 56.3 mmol) was added to the mixture, and the resulting solution was stirred at 50° C. for 1 hour. And then the product was filtered, washed, and dried to prepare 6-(pyridine-2-ylmethoxy)-pyridine-3-ylamine (3.42 g, 100%).

The 6-(pyridine-5-ylmethoxy)-pyridine-3-ylamine (114 mg, 0.57 mmol) and indole-3-carboxylic acid (91 mg, 0.57 mmol) were dissolved in DMF (3 ml), DCC (117 mg, 0.57 mmol) was added to the solution, and then the mixture was stirred at 80° C. for 8 hours. After the reaction was completed, the product was washed and filtered to yield a target compound as a white solid (44 mg, 23%) by chromatography (methanol:dichloromethane=2:30).

Example 21

Preparation of 1H-indole-3-carboxylic acid[6-(6-methyl-pyridine-3-yloxy)-pyridine-3-yl]-amide

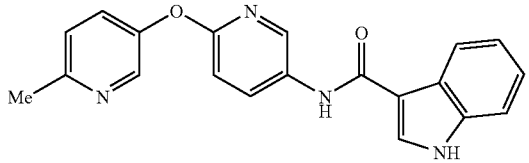

6-methylpyridine-3-ol (1.0 g, 9.16 mmol) was dissolved in is DMF (20 ml), and the solution was stirred with NaH (230 mg, 9.6 mmol) and 2-chloro-5-nitro pyridine (1.45 g, 9.16 mmol) at room temperature for 1 hour. Subsequently, the product was filtered, washed, and dried under reduced pressures to yield a solid product (2.08 g, 98%). The solid product (1.0 g, 4.32 mmol) was added to a mixed solution of ethanol (80 ml) and conc. hydrochloric-acid (20 ml), SnCl$_2$ (2.9 g, 15.12 mmol) was added to the mixture, and the resulting solution was stirred at 50° C. for 1 hour. And then the product was filtered, washed, and dried to prepare 6-(6-methylpyridine-3-yloxy)-pyridine-3-amine (0.73 g, 84%).

The 6-(6-methylpyridine-3-yloxy)-pyridine-3-amine (300 mg, 1.49 mmol) and indole-3-carboxylic acid (240 mg, 1.49 mmol) were dissolved in DMF (10 ml), DCC (280 mg, 1.49 mmol) was added to the solution, and then the mixture was stirred at 80° C. for 3 hours. After the reaction was completed, the product was washed and filtered to yield a target compound as a grey solid (340 mg, 66%) by chromatography (methanol:dichloromethane=1:30).

Example 22

Preparation of 1H-indole-3-carboxylic acid[6-(2-chloro-pyridine-3-yloxy)-pyridine-3-yl]-amide

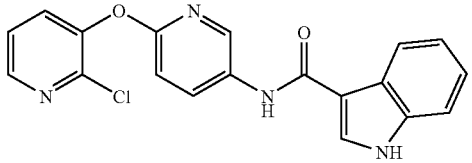

2-chloropyridine-3-ol (1.0 g, 7.72 mmol) was dissolved in DMF (20 ml), and the solution was stirred with NaH (200 mg, 8.1 mmol) and 2-chloro-5-nitro pyridine (1.2 g, 7.72 mmol) at room temperature for 1 hour. Subsequently, the product was filtered, washed, and dried under reduced pressures to yield a solid product (1.88 g, 97%). The solid product (1.80 g, 7.15 mmol) was added to a mixed solution of ethanol (20 ml) and conc. hydrochloric acid (5 ml), SnCl2 (4.06 g, 21.45 mmol) was added to the mixture, and the resulting solution was stirred at 50° C. for 1 hour. And then the product was filtered, washed, and dried to prepare 6-(2-chloropyridine-3-yloxy)-pyridine-3-amine (1.42 g, 90%).

The 6-(2-chloropyridine-3-yloxy)-pyridine-3-amine (200 mg, 0.9 mmol) and indole-3-carboxylic acid (150 mg, 0.9 mmol) were dissolved in DMF (5 ml), DCC (200 mg, 0.99 mmol) was added to the solution, and then the mixture was stirred at 70° C. for 8 hours. After the reaction was completed, the product was washed and filtered to yield a target compound as a white solid (200 mg, 61%) by chromatography (methanol:dichloromethane=1:30).

Example 23

Preparation of 1H-indole-3-carboxylic acid[6-(2-bromo-pyridine-3-yloxy)-pyridine-3-yl]-amide

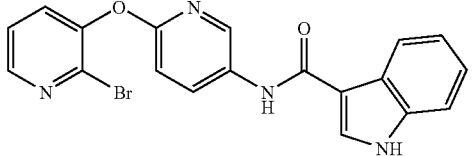

2-bromopyridine-3-ol (1.0 g, 5.75 mmol) was dissolved in DMF (20 ml), and the solution was stirred with NaH (242 mg, 6.04 mmol) and 2-chloro-5-nitro pyridine (0.9 g, 5.75 mmol) at room temperature for 8 hours. Subsequently, the product was filtered, washed, and dried under reduced pressures to yield a solid product (1.7 g, 99%). The solid product (1.5 g, 5.08 mmol) was added to a mixed solution of ethanol (20 ml) and conc. hydrochloric acid (5 ml), SnCl2 (2.19 g, 15.2 mmol) was added to the mixture, and the resulting solution was stirred at 50° C. for 3 hours. And then the product was filtered, washed, and dried to prepare 6-(2-bromopyridine-3-yloxy)pyridine-3-amine (1.11 g, 82%)

The 6-(2-bromopyridine-3-yloxy)pyridine-3-amine (200 ml, 1.24 mmol) and indole-3-carboxylic acid (200 mg, 1.24 mmol) were dissolved in DMF (5 ml), DCC (280 mg, 1.37 mmol) was added to the solution, and then the mixture was stirred at 60° C. for 8 hours. After the reaction was completed, the product was washed and filtered to yield a target compound as a white solid (100 mg, 20%) by chromatography (methanol:dichloromethane=1:30).

Example 24

Preparation of 1H-indole-3-carboxylic acid[6-(pyridine-3-yloxy)-pyridine-3-yl]-amide

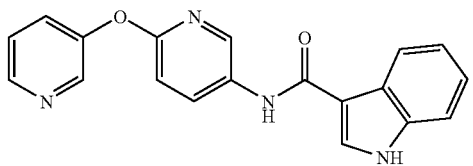

Pyridine-3-ol (1.0 g, 10.51 mmol) was dissolved in DMF (20 ml), and the solution was stirred with NaH (422 mg, 10.51 mmol) and 2-chloro-5-nitro pyridine (1.7 g, 10.51 mmol) at room temperature for 8 hours. Subsequently, the product was filtered, washed, and dried under reduced pressures to yield a solid product (2.0 g, 88%). The solid product (1.6 g, 7.37 mmol) was added to a mixed solution of ethanol (20 ml) and conc. hydrochloric acid (5 ml), SnCl2 (4.19 g, 22.11 mmol) was added to the mixture, and the resulting solution was stirred at 50° C. for 3 hours. And then the product was filtered, washed, and dried to prepare 6-(pyridine-3-yloxy)pyridine-3-amine (1.24 g, 90%).

The 6-(pyridine-3-yloxy)pyridine-3-amine (200 mg, 1.24 mmol) and indole-3-carboxylic acid (200 mg, 1.24 mmol) were dissolved in DMF (5 ml), DCC (280 mg, 1.37 mmol) was added to the solution, and then the mixture was stirred at 60° C. for 8 hours. After the reaction was completed, the product was washed and filtered to yield a target compound as a white solid (250 mg, 61%) by chromatography (methanol:dichloromethane=1:30).

Example 25

Preparation of 1H-indole-3-carboxylic acid(6-phenoxy-pyridine-3-yl)-amide

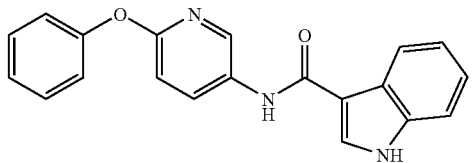

Phenol (1.0 g, 10.6 mmol) was dissolved in DMF (20 ml), and the solution was stirred with NaH (430 mg, 10.51 mmol) and 2-chloro-5-nitro pyridine (1.68 g, 10.6 mmol) at room temperature for 8 hours. Subsequently, the product was filtered, washed, and dried under reduced pressures to yield a solid product (1.7 g, 99%). The solid product (2.0 g, 9.25 mmol) was added to a mixed solution of ethanol (20 ml) and conc. hydrochloric acid (5 ml), SnCl2 (5.26 g, 27.75 mmol) was added to the mixture, and the resulting solution was stirred at 50° C. for 3 hours. And then the product was filtered, washed, and dried to prepare 6-phenoxypyridine-3-amine (1.5 g, 87%).

The 6-phenoxypyridine-3-amine (200 mg, 1.07 mmol) and indole-3-carboxylic acid (200 mg, 1.07 mmol) were dissolved in DMF (5 ml), DCC (200 mg, 1.07 mmol) was added to the solution, and then the mixture was stirred at 60° C. for 8 hours. After the reaction was completed, the product was washed and filtered to yield a target compound as a white solid (60 mg, 17%) by chromatography (methanol:dichloromethane=1:30).

Example 26

Preparation of 1H-indole-3-carboxylic acid pyridine-3-ylamide

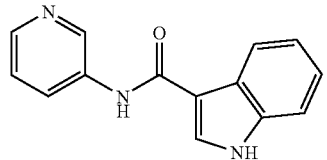

3-aminopyridine (290 mg, 3.1 mmol) and indole-3-carboxylic acid (500 mg, 3.1 mmol) was dissolved in DMF (20 ml), DCC (579 mg, 3.1 mmol) was added to the solution, and then the mixture was stirred at 60° C. for 8 hours. After the reaction was completed, the product was washed and filtered to yield a target compound as a white solid (300 mg, 42%) by chromatography (methanol:dichloromethane=1:20).

Example 27

Preparation of 1H-indole-3-carboxylic acid (4-pyridine-3-yl-phenyl)-amide

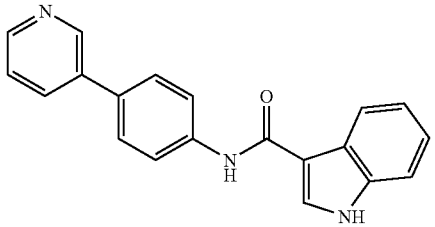

3-pyridineboronic acid (0.3 g, 2.44 mmol), 1-iodo-3-nitrobenzene (0.61 g, 2.44 mmol), sodium carbonate (0.78 g, 7.32 mmol), and Pd(PPh3)4 (0.28 g, 0.24 mmol) were dissolved in a mixed solvent of 1,2-dimethoxyethane (50 ml) and water (13 ml), and the solution was refluxed for 12 hours. Subsequently, the product was filtered, washed, and dried under reduced pressures to yield a solid product. The solid product was added to a mixed solution of ethanol (20 ml) and conc. hydrochloric acid (6 ml), SnCl2 (1.92 g, 10.13 mmol) was added to the mixture, and the resulting solution was stirred at 60° C. for 1 hour. And then the product was filtered, washed, and dried to prepare 3-pyridine-3-yl-phenylamine.

The crude 3-pyridine-3-yl-phenylamine (60 mg, 0.35 mmol) and indole-3-carboxylic acid (57 mg, 0.35 mmol)

were dissolved in DMF (3 ml), DCC (73 mg, 0.35 mmol) was added to the solution, and then the mixture was stirred at 80° C. for 8 hours. After the reaction was completed, the product was washed and filtered to yield a target compound as a white solid (60 mg, 55%) by chromatography (methanol:dichloromethane=1:20).

Example 28

Preparation of 6-methyl-1H-indole-3-carboxylic acid [6-(2-chloro-pyridine-3-yloxy)-pyridine-3-yl]-amide

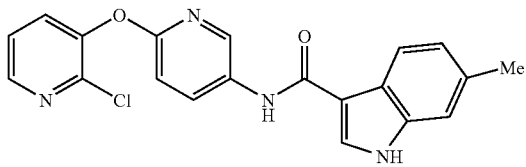

The 6-methyl-1H-indole-3-carboxylic acid (50 mg, 0.28 mmol) in Example 16 and the 6-(2-chloropyridine-3-yloxy)-pyridine-3-amine (60 mg, 0.28 mmol) in Example 22 were dissolved in DMF (5 ml), HBTU (100 mg, 0.28 mmol) and triethylamine (0.11 ml, 0.84 mmol) were added to the solution, and the mixture was stirred at 80° C. for 8 hours. After the reaction was completed, the product was washed and filtered to yield a target compound as a white solid (18 ml, 34%) by chromatography (methanol:dichloroinethane=1:30).

Example 29

Preparation of 1H-indole-3-carboxylic acid[4-(4,6-dimethoxy-[1,3,5]triazine-2-ylxoxy)-phenyl]-amide

4-nitrophenol (1.0 g, 7.2 mmol) was dissolved in DMF (30 ml), and the solution was stirred with NaH (290 mg, 7.2 mmol) and 2-chloro-4,6-dimethoxytriazine (3.19 g, 20.1 mmol) at room temperature for 3 hours. Subsequently, the product was filtered, washed, and dried under reduced pressures to yield a liquid product (1.54 g, 75%). The liquid product (1.0 g, 3.6 mmol) was added to a mixed solution of THF (20 ml), water (2 ml), and acetic acid (1.7 ml), Fe (1.98 g, 36 mmol) was added to the mixture, and the resulting solution was stirred at 70° C. for 12 hours. And then the product was filtered, washed, and dried to prepare 4-(4,6-dimethoxy-[1,3,5]triazine-2-yloxy)-phenylamine (0.89 g, 91%).

The 4-(4,6-dimethoxy-[1,3,5]triazine-2-yloxy)-phenylamine (213 mg, 0.86 mmol) and indole-3-carboxylic acid (58 mg, 0.86 mmol) were dissolved in DMF (5 ml), DCC (74 mg, 0.86 mmol) was added to the solution, and then the mixture was stirred at 80° C. for 8 hours. After the reaction was completed, the product was washed and filtered to yield a target compound as a white solid (110 mg, 33%) by chromatography (methanol:dichloromethane=1:30).

The state, yield, melting point, and 1H NMR of piperidine derivatives represented by Formula (1), obtained by methods in Examples of the present invention are summarized in Table 1, below.

TABLE 1

| Classification | state | Yield (%) | mp (° C.) | MS (EI) | $^1$H NMR Data |
|---|---|---|---|---|---|
| Example 1 | yellow solid | 23 | 128-129 | m/e 381.1 [M]$^+$ | $^1$H NMR (200 MHz, CDCl$_3$) δ 2.47 (s, 3H, CH$_3$), 7.00 (d, J = 8.6 Hz, 1H, ArH), 7.18-7.34 (m, 2H, ArH), 7.43 (m, 3H, ArH), 7.61-7.78 (m, 3H, ArH), 8.15 (s, 1H, NH), 8.39 (s, 1H, ArH), 8.45 (s, 1H, ArH) |
| Example 2 | white solid | 66 | 93-95 | m/e 397.1 [M]$^+$ | $^1$H NMR (200 MHz, CDCl$_3$) δ 2.40 (s, 3H, CH$_3$), 7.29-7.56 (m, 7H, ArH), 7.90 (d, J = 7.2 Hz, 3H, ArH), 8.48 (s, 1H, ArH) |
| Example 3 | white solid | 10 | 52-55 | m/e 346.11 [M + H]$^+$ | $^1$H NMR (200 MHz, CDCl$_3$) δ 2.44 (s, 3H, CH$_3$), 6.99 (d, J = 8.6 Hz, 1H, ArH), 7.18-7.26 (m, 1H, ArH), 7.33-743 (m, 3H, ArH), 7.54-7.58 (m, 1H, NH), 8.0-8.05 (m, 1H, ArH), 8.14 (s, 1H, ArH), 8.24-8.30 (m, 3H, ArH), 8.38-8.40 (m, 1H, NH) |
| Example 4 | white solid | 58 | 81-83 | m/e 361.1 [M]$^+$ | $^1$H NMR (200 MHz, CDCl$_3$) δ 2.46 (s, 3H, CH$_3$), 7.03 (d, J = 8.9 Hz, 1H, ArH), 7.18 (m, 1H, ArH), 7.45 (m, 3H, ArH), 7.79 (s, 1H, ArH), 7.90 (m, 1H, ArH), 8.04 (s, 1H, NH), 8.20 (d, J = 2.4 Hz, 1H, ArH), 8.30 (m, 1H, ArH), 8.40 (m, 2H, ArH) |
| Example 5 | brown solid | 14 | 215-217 | m/e 344.08 [M + H]$^+$ | $^1$H NMR (200 MHz, CDCl$_3$) δ 2.45 (s, 3H, CH$_3$), 6.96-7.01 (m, 1H, ArH), 7.10-7.48 (m, 7H, ArH), 7.67 (d, J = 7.6 Hz, 1H, ArH), 8.29-8.37 (m, 3H, ArH) |
| Example 6 | yellow solid | 47 | 108-110 | m/e 344.1 [M]$^+$ | $^1$H NMR (200 MHz, CDCl$_3$) δ 2.46 (s, 3H, CH$_3$), 7.00 (d, J = 8.95 Hz, 1H, ArH), 7.32 (m, 4H, ArH), 7.70 (br s, 1H, NH), 7.90 (d, J = 2.85 Hz, 1H, ArH), 8.05 (m, 1H, ArH), 8.21 (d, J = 2.44 Hz, 1H, ArH), 8.31 (dc, J = 2.64, 8.75 Hz, 1H, ArH), 8.37 (d, J = 4.48 Hz, ArH), 8.80 (br s, 1H, NH) |
| Example 7 | white solid | 86 | 191-193 | m/e 345.0 [M]$^+$ | $^1$H NMR (300 MHz, d$_6$-DMSO) δ 2.33 (s, 3H, CH$_3$), 7.19 (d, J = 8.88 Hz, 1H, ArH), 7.33 (m, 3H, ArH), 7.53 (dd, J = 1.38, 8.13 Hz, 1H, ArH), 7.70 (br s, 1H, ArH), 8.48 (m, 2H, ArH), 8.63 (s, 1H, ArH) |
| Example 8 | brown solid | 10 | 156-158 | m/e 356.08 [M + H]$^+$ | $^1$H NMR (200 MHz, CDCl$_3$) δ 2.46 (s, 3H, CH$_3$), 7.03 (d, J = 8.4 Hz, 1H, ArH), 7.18-7.27 (m, 2H, ArH), 7.40 (d, J = 8.2 Hz, |

TABLE 1-continued

| Classification | state | Yield (%) | mp (° C.) | MS (EI) | ¹H NMR Data |
|---|---|---|---|---|---|
| | | | | | 1H, ArH), 7.60 (t, J = 3.6 Hz, 3H, ArH), 7.90-8.06 (m, 1H, ArH), 8.27-8.41 (m, 5H, ArH) |
| Example 9 | colorless liquid | 19 | | m/e 331.09 [M + H]⁺ | ¹H NMR (200 MHz, CDCl₃) d 2.49 (s, 3H, CH₃), 4.46 (s, 2H, CH₂), 6.83 (m, 1H, ArH), 6.99-7.41 (m, 7H, ArH), 7.65 (m, 2H, ArH), 8.29 (m, 1H, ArH), 8.39 (br s, 1H, NH) |
| Example 10 | white solid | 89 | 120-123 | m/e 360.4 [M]⁺ | ¹H NMR (200 MHz, CDCl₃) d 2.47 (s, 3H, CH₃), 7.00 (d, J = 8.6 Hz, 1H, ArH), 7.21-7.46 (m, 5H, ArH), 7.66 (s, 1H, NH), 7.90 (d, J = 2.8 Hz, 1H, ArH), 8.05 (m, 1H, ArH), 8.21-8.40 (m, 3H, ArH), 8.73 (s, 1H, NH) |
| Example 11 | white solid | 90 | 255-257 | m/e 358.2 [M]⁺ | ¹H NMR (200 MHz, CDCl₃) d 2.47 (s, 3H, CH₃), 3.83 (s, 3H, NCH₃), 7.00 (d, J = 8.6 Hz, 1H, ArH), 7.20-7.41 (m, 5H, ArH), 7.60 (s, 1H, NH), 7.70 (s, 1H, ArH), 8.02 (m, 1H, ArH), 8.20 (d, J = 2.4 Hz, 1H, ArH), 8.30 (d, J = 9.0 Hz, 1H, ArH), 8.40 (d, J = 1.6 Hz, 1H, ArH) |
| Example 12 | white solid | 90 | 95-96 | m/e 358.2 [M]⁺ | ¹H NMR (300 MHz, d₆-DMSO) d 2.35 (s, 3H, CH₃), 3.50 (s, 3H, NCH₃), 6.76 (d, J = 2.8 Hz, 1H, ArH), 6.90 (d, J = 9.0 Hz, 1H, ArH), 7.27 (m, 5H, ArH), 7.60 (d, J = 6.2 Hz, 1H, ArH), 7.98 (m, 2H, ArH), 8.37 (d, J = 3.2 Hz, 1H, ArH) |
| Example 13 | brown solid | 12 | 116-118 | m/e 372.2 [M]⁺ | ¹H NMR (200 MHz, CDCl₃) d 2.35 (s, 3H, CH₃), 2.50 (s, 3H, NCH₃), 3.65 (s, 3H, NCH₃), 6.63 (s,, 1H, ArH), 6.90 (d, J = 8.8 Hz, 1H, ArH), 7.19 (m, 4H, ArH), 7.36 (d, J = 7.0 Hz, 1H, ArH), 7.63 (d, J = 3.0 Hz, 1H, ArH), 7.90 (d, J = 7.6 Hz, 1H, ArH), 8.00 (d, J = 2.4 Hz, 1H, ArH), 8.37 (d, J = 3.6 Hz, 1H, ArH) |
| Example 14 | white solid | 44 | 244-245 | m/e 359.10 [M + H]⁺ | ¹H NMR (200 MHz, CDCl₃) d 2.46 (s, 3H, CH₃), 2.47 (s, 3H, CH₃), 6.96 (d, J = 8.6 Hz, 1H, ArH), 7.07 (d, J = 8.2 Hz, 1H, ArH), 7.23-7.43 (m, 4H, ArH), 7.95 (d, J = 13.4 Hz, 2H, ArH), 8.28 (d, J = 6.6 Hz, 2H, ArH) |
| Example 15 | colorless liquid | $ $ | | m/e 375.02 [M + H]⁺ | ¹H NMR (200 MHz, CDCl₃) d 2.37 (s, 3H, CH₃), 3.77 (s, 3H, OMc), 6.84-6.92 (m, 2H, ArH), 7.09-7.13 (m, 1H, ArH), 7.20-7.32 (m, 1H, ArH), 7.67 (d, J = 13.8 Hz, 2H, ArH), 8.14-8.28 (m, 4H, ArH) 8.41 (s, 1H, NH), 9.67 (s, 1H, NH) |
| Example 16 | white solid | 45 | 203-206 | m/e 359.09 [M + H]⁺ | ¹H NMR (200 MHz, CDCl₃) d 2.45 (s, 3H, CH₃), 2.48 (s, 3H, CH₃), 6.98 (d, J = 8.8 Hz, 1H, ArH), 7.12-7.26 (m, 2H, ArH), 7.20 (d, J = 8.1 Hz, 1H, ArH), 7.80 (d, J = 2.8 Hz, 2H, ArH), 7.90 (d, J = 8 Hz, 1H, ArH), 8.19-8.38 (m, 3H, ArH) |
| Example 17 | white solid | 7 | 204-207 | m/e 359.09 [M + H]⁺ | ¹H NMR (200 MHz, CDCl₃) d 2.47 (s, 3H, CH₃), 2.65 (s, 3H, CH₃), 7.00 (d, J = 9 Hz, 1H, ArH), 7.11-7.29 (m, 2H, ArH), 7.40 (d, J = 8 Hz, 1H, ArH), 7.65 (s, 1H, ArH), 7.86 (d, J = 7.8 Hz, 1H, ArH), 7.92 (d, J = 2.8 Hz, 1H, ArH), 8.21 (d, J = 2.4 Hz, 1H, NH), 8.31 (d, J = 6 Hz, 1H, ArH), 8.38 (d, J = 4.4 Hz, 1H, ArH), 8.63 (s, 1H, NH) |
| Example 18 | white solid | 11 | 230-232 | m/e 470.0 [M]⁺ | ¹H NMR (200 MHz, CDCl₃) d 2.46 (s, 3H, CH₃), 7.0 (d, J = 8.4 Hz, 1H, ArH), 7.21 (d, J = 2.8 Hz, 1H, ArH), 7.27 (d, J = 5.2 Hz, 1H, ArH), 7.45 (m, 3H, ArH), 7.95 (s, 1H, ArH), 8.31 (m, 3H, ArH), 8.61 (d, J = 7.2 Hz, 1H, ArH) |
| Example 19 | white solid | 59 | 134-137 | m/e 331.2 [M]⁺, 302.1, 275.1 | ¹H NMR (200 MHz, d₆-DMSO) d 7.20 (m, 4H, ArH), 7.46 (d, J = 8.1 Hz, 1H, ArH), 8.15 (d, J = 6.9 Hz, 1H, ArH), 8.30 (m, 2H, ArH), 8.47 (s, 1H, ArH), 8.75 (s, 1H, ArH), 9.04 (s, 1H, ArH), 9.95 (s, 1H, NH), 11.79 (s, 1H, NH) |
| Example 20 | white solid | 23 | 220-222 | m/e 344.1 [M]⁺, 327.2, 297.2 | ¹H NMR (200 MHz, d₆-DMSO) d 5.40 (s, 2H, CH₂), 6.95 (d, J = 9.4 Hz, 1H, ArH), 7.15 (m, 2H, ArH), 7.33 (m, 1H, ArH), 7.44 (m, 2H, ArH), 7.78 (m, 1H, ArH), 8.11 (m, 2H, ArH), 8.24 (s, 1H, ArH), 8.45 (d, J = 2.8 Hz, 1H, ArH), 8.55 (d, J = 4.9 Hz, 1H, ArH), 9.78 (s, 1H, NH), 11.74 (s, 1H, NH) |
| Example 21 | gray solid | 66 | 109-110 | m/e 344.1 [M]⁺ | ¹H NMR (200 MHz, CDCl₃) d 2.50 (s, 3H, CH₃), 6.90 (d, J = 8.2 Hz, 1H, ArH), 7.11 (d, J = 8.2 Hz, 1H, ArH), 7.29 (m, 3H, ArH), 7.80 (s, 1H, ArH), 8.13 (m, 4H, ArH), 8.31 (s, 1H, ArH) |
| Example 22 | white solid | 61 | 191-192 | m/e 365.07 [M + H]⁺ | ¹H NMR (200 MHz, CDCl₃) d 7.07 (d, J = 9.1 Hz, 1H, ArH), 7.24-7.48 (m, 5H, ArH), 7.60 (d, J = 6.6 Hz, 1H, ArH), 7.97 (s, 1H, NH), 8.14-8.37 (m, 3H, ArH), 8.37 (d, 1H, ArH), 8.96 (s, 1H, NH) |
| Example 23 | white solid | 20 | 173-180 | m/e 410.84 [M + H] | ¹H NMR (200 MHz, CDCl₃) d 7.05 (d, J = 8.6 Hz, 1H, ArH), 7.24-7.54 (m, 6H, ArH), 7.93 (s, 1H, ArH), 8.16 (s, 1H, ArH), 8.24 (s, 1H, ArH), 8.34 (d, J = 9 Hz, 1H, ArH) |
| Example 24 | white solid | 61 | 106-109 | m/e 331.15 [M + H]⁺ | ¹H NMR (200 MHz, CDCl₃) d 7.03 (d, J = 8.6 Hz, 1H, ArH), 7.31-7.34 (m, 3H, ArH), 7.49-7.53 (m, 2H, ArH), 7.85 (d, J = 14.4 Hz, 2H, ArH), 8.05 (s, 1H, NH), 8.29 (d, J = 9 Hz, 2H, ArH), 8.48 (d, J = 10.6 Hz, 2H, ArH), 8.9 (s, 1H, NH) |
| Example 25 | white solid | 17 | 205-206 | m/e 330.34 [M + H]⁺ | ¹H NMR (200 MHz, CDCl₃) d 6.94 (d, J = 6.6 Hz, 1H, ArH), 7.11-7.49 (m, 8H, ArH), 7.98 (s, 1H, ArH), 8.17 (t, J = 3.4 Hz, 1H, ArH), 8.23 (s, 1H, ArH), 8.39 (d, J = 9 Hz, 1H, ArH) |

TABLE 1-continued

| Classification | state | Yield (%) | mp (° C.) | MS (EI) | $^1$H NMR Data |
|---|---|---|---|---|---|
| Example 26 | white solid | 42 | 236-239 | m/e 238.14 [M + H]$^+$ | $^1$H NMR (200 MHz, CDCl$_3$) d 7.27-7.49 (m, 4H, ArH), 7.98 (s, 1H, ArH), 8.16 (t, J = 3.4 Hz, 1H, ArH), 8.28 (d, J = 4.6 Hz, 1H, ArH), 8.43 (d, J = 8.4 Hz, 1H, ArH), 8.60 (s, 1H, ArH) |
| Example 27 | white solid | 55 | 69-71 | m/e 313.1 [M]$^+$, 284.1, 257.1 | $^1$H NMR (300 MHz, d$_6$-DMSO) d 7.18 (m, 2H, ArH), 7.40 (d, J = 7.8 Hz, 1H, ArH), 7.50 (m, 4H, ArH), 7.83 (d, J = 8.4 Hz, 1H, ArH), 8.06 (s, 1H, ArH), 8.09 (d, J = 1.9 Hz, 1H, ArH), 8.19 (d, J = 6.6 Hz, 1H, ArH), 8.30 (s, 1H, ArH), 8.58 (d, J = 3.3 Hz, 1H, ArH), 8.86 (d, J = 1.9 Hz, 1H, NH), 9.91 (s, 1H, NH) |
| Example 28 | white solid | 34 | 186-200 | m/e 379.10 [M + H]$^+$ | $^1$H NMR (300 MHz, CDCl$_3$) d 2.50 (d, J = 8.7 Hz, 1H, ArH), 7.10 (d, J = 8.1 Hz, 1H, ArH), 7.15 (t, J = 2.4 Hz, 2H, ArH), 7.60 (d, J = 6.6 Hz, 1H, ArH), 7.68 (s, 1H, NH), 7.89 (d, J = 2.7 Hz, 1H, ArH), 7.90 (d, J = 8.1 Hz, 1H, ArH), 8.20 (d, J = 2.1 Hz, 1H, ArH), 8.27-8.34 (m, 2H, ArH), 8.50 (s, 1H, NH) |
| Example 29 | white solid | 33 | 212-216 | m/e 391.1 [M]$^+$, 361.2, 283.1 | $^1$H NMR (200 MHz, d$_6$-DMSO) d 3.89 (s, 6H, CH$_3$ × 2), 7.19 (m, 4H, ArH), 7.46 (d, J = 6.9 Hz, 1H, ArH), 7.81 (d, J = 8.9 Hz, 2H, ArH), 8.17 (m, 1H, ArH), 8.28 (s, 1H, ArH), 9.91 (s, 1H, NH), 11.74 (s, 1H, NH) |

Comparative Example 1

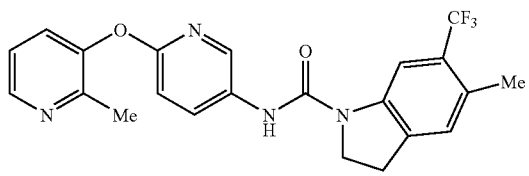

SB-243213, a conventional 5-HT$_{2c}$ receptor antagonist, was prepared using methods in Bromidge, S. M.; Dabbs, S.; Davies, D. T.; Davies, S.; Duckworth, D. M.; Forbes, I. T.; Gaster, L. M.; Ham, P.; Jones, G. E.; King, F. D.; Mulholland, K. R.; Saunders, D. V.; Wyman, P. A.; Blaney, F. E.; Clarke, S. E.; Blackburn, Thomas P.; Holland, V.; Kennett, G. A.; Lightowler, S.; Middlemiss, D. N.; Trail, B.; Riley, G. J.; Wood, M. D. J. Med. Chem. 2000, 43, 1123.

State: white solid mp: 212-214° C.

1H NMR (300 MHz, CDCl3) δ 2.43 (s, 3H, CH3), 2.45 (s, 3H, CH3), 3.28 (t, J=8.5 Hz, 2H, CH2), 4.13 (t, J=8.6 Hz, 2H, CH2), 6.37 (s, 1H, NH), 6.98 (d, J=8.8 Hz, 1H, ArH), 7.09 (s, 1H, ArH), 7.19 (m, 1H, ArH), 7.38 (dd, J=1.4, 8.1 Hz, 1H, ArH), 7.99 (d, J=2.9 Hz, 1H, ArH), 8.09 (dd, J=1.4, 8.8 Hz, 1H, ArH), 8.23 (s, 1H, ArH), 8.37 (dd, J=1.5, 4.8 Hz, 1H, ArH);

MS(EI) m/e 428[M]+, 413, 385.

Comparative Example 2

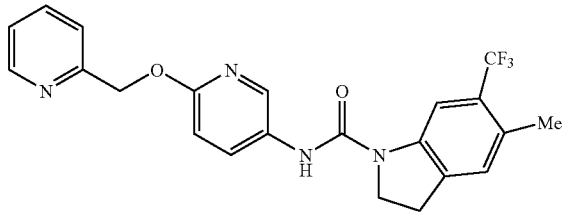

SB-247853, a conventional 5-HT$_{2c}$ receptor antagonist, was prepared using methods in Bromidge, S. M.; Davies, S.; Duckworth, D. M.; Forbes, I. T.; Jones, G. E.; Jones, J.; King, F. D.; Blackburn, T. P.; Holland, V.; Kennett, G. A.; Lightowler, S.; Middlemiss, D. N.; Riley, G. J.; Trail, B.; Wood, M. D. Bioorg. Med. Chem. Lett. 2000, 10, 1867.

State: white solid mp: 220-222° C.

1H NMR (200 MHz, CDCl3) δ 2.42 (s, 3H, CH3), 3.28 (t, J=8.5 Hz, 2H, CH2), 4.13 (t, J=8.7 Hz, 2H, CH2), 5.5 (s, 2H, CH2), 6.27 (s, 1H, NH), 6.90 (d, J=8.5 Hz, 1H, ArH), 7.08 (s, 1H, ArH), 7.22 (m, 1H, ArH), 7.45 (d, J=7.7 Hz, 1H, ArH), 7.71 (m, 1H, ArH), 7.91 (dd, J=2.9, 9.0 Hz, 1H, ArH), 8.23 (s, 1H, ArH), 8.60 (m, 1H, ArH);

MS(EI) m/e 428[M]+, 411, 378.

Experimental Example 1

Experimental of Binding Affinity to the Serotonin 5-HT$_{2c}$ Receptor

In order to see the binding affinity of derivatives of the present invention to serotonin 5-HT$_{2c}$ receptors, the following experiment was performed.

As a receptor, a human gene recombinant 5-HT$_{2c}$ receptor expressed in CHO—K1 cell was purchased from Euroscreen, Belgium and used in the experiment, and as a radioactive isotope, [3H]mesulergine (Amersham Biosciences, UK).

A final volume of 0.25 ml reaction mixture was prepared by adding 50 mM Tris-HCl buffer (pH 7.7) containing one of the compounds in Examples 1-29 or Comparative Examples 1-2, 1 nM of [3H]mesulergine, 5-HT$_{2c}$ receptor membranes (4 D/well), 0.1% ascorbic acid and 10 M pargyline, and incubated at 37° C. for 30 minutes. After incubation, the reaction was terminated by the rapid filtration using an Inotech harvester (Inotech) through a Wallace GF/C glass fiber filter (Wallac, Finland) which was presoaked in 1% BSA, and then washed with ice-cold 50 mM Tris-HCl buffer. The filter was covered with MeltiLex, sealed in a sample bag followed by drying in the oven, and counted by MicroBeta Plus (Wallac). Non-specific binding was determined in the presence of 0.5 M Mianserin. Three repeating experiments were carried out with 7-8 concentrations of the compound in Examples 1-29 or the compound in comparative examples 1-2, run in duplicate tubes, and isotherms from the three assays were calculated by a nonlinear regression analysis (GraphPad Prism Program, San Diego, USA) to yield IC$_{50}$ values. The lower the IC$_{50}$ values are indicates that the affinity for the 5-HT$_{2c}$ receptors is higher.

The experimental results are summarized in Table 2.

TABLE 2

| Division | IC$_{50}$ (nM) |
|---|---|
| Example 1 | 321 |
| Example 2 | 572 |
| Example 3 | 167 |
| Example 4 | 50 |
| Example 5 | 59 |
| Example 6 | 67 |
| Example 7 | >10000 |
| Example 8 | 302 |
| Example 9 | >10000 |

TABLE 2-continued

| Division | IC$_{50}$ (nM) |
|---|---|
| Example 10 | 23 |
| Example 11 | 474 |
| Example 12 | 9441 |
| Example 13 | 6369 |
| Example 14 | 4.5 |
| Example 15 | 10.7 |
| Example 16 | 1.9 |
| Example 17 | 8.2 |
| Example 18 | 0.6 |
| Example 19 | 50 |
| Example 20 | 5.9 |
| Example 21 | 2253 |
| Example 22 | 0.5 |
| Example 23 | 106 |
| Example 24 | 1.6 |
| Example 25 | 542 |
| Example 26 | >1000 |
| Example 27 | 214 |
| Example 28 | 7 |
| Example 29 | >10000 |
| Comparative Example 1 | 0.7 |
| Comparative Example 2 | 1.3 |

As shown in Table 2, it was identified that compounds according to the present invention had IC$_{50}$ values equivalent to or better than those of conventional 5-HT$_{2c}$ receptor inhibitors (Comparative Examples 1 and 2). In particular, the compounds in Example 18 and 22 have lower IC$_{50}$ values than those in Comparative Examples. From these, compounds according to the present invention have high affinities for 5-HT$_{2c}$ receptors, relatively inhibit serotonin from binding to 5-HT$_{2c}$ receptors, and thus may prevent or treat diseases caused by serotonin which is excessively bound to the 5-HT$_{2c}$ receptors.

Experimental Example 2

Experiment of serotonin 5-HT$_{2c}$ Receptor Selectivity

In order to understand whether derivatives according to the present invention selectively bind to serotonin 5-HT$_{2c}$ receptors, the following experiment was performed.

For their high binding affinities for 5-HT$_{2c}$, compounds in Examples 14 to 18, 20, and 22 or in Comparative Example 1 were used for the experiment with reaction mixtures. Except that CNS receptors such as 5-HT$_{1a}$, 5-HT$_{2a}$, 5-HT$_7$, D$_2$, D$_3$ or D$_4$ other than 5-HT$_{2c}$ were used as a receptor, IC$_{50}$ values (nM) were measured in the same manner as in Experimental Example 1.

Results of measurements were shown in Table 3.

TABLE 3

| Division | 5-HT$_{2c}$ | 5-HT$_{1a}$ | 5-HT$_{2a}$ | 5-HT$_6$ | 5-HT$_7$ | D$_2$ | D$_3$ | D$_4$ |
|---|---|---|---|---|---|---|---|---|
| Example 14 | 4.5 | >10000 | >1000 | >10000 | >10000 | >10000 | >10000 | >10000 |
| Example 15 | 10.7 | >10000 | >10000 | >10000 | >10000 | >10000 | >10000 | >10000 |
| Example 16 | 1.9 | >10000 | >10000 | >10000 | >10000 | >10000 | >10000 | >10000 |
| Example 17 | 8.2 | >10000 | >10000 | >10000 | >10000 | >10000 | >10000 | >10000 |
| Example 18 | 0.62 | 780 | 84.7 | >1000 | >1000 | >10000 | >1000 | >1000 |
| Example 20 | 5.9 | >10000 | >10000 | >1000 | >10000 | >10000 | >10000 | >10000 |
| Example 22 | 0.5 | >10000 | >1000 | >10000 | >10000 | >10000 | >10000 | >1000 |
| Comparative Example 1 | 0.7 | >1000 | 32.4 | 667 | >1000 | >1000 | >1000 | >10000 |

AS shown in Table 3, derivatives according to the present invention have high affinities as the IC$_{50}$ values for 5-HT$_{2c}$ are 0.5 to 10.7 nM, while values for other receptors (5-HT$_{1a}$, 5-HT$_{2a}$, 5-HT$_6$, 5-HT$_7$, D$_2$, D$_3$, and D$_4$) are more than 1000 meaning that they are rarely bound to the receptors. Thus, derivatives according to the present invention selectively bind to 5-HT$_{2c}$ receptors, rarely have adverse effects caused by binding to other receptors, and may prevent or treat diseases caused by serotonin which is excessively bound to the 5-HT$_{2c}$ receptors.

Experimental Example 3

In vitro Functional Experiment

In order to identify whether derivatives according to the present invention have antagonist activities for G proteins binding to 5-HT$_{2c}$ receptors, the following experiment was performed.

The experiment was carried out by known methods in Sim, L. et al, Proc. Natl. Acad. Sci. USA, 1995, 92, 7242, using DSPS (MDS Pharma Services PT#1102941), and [$^{35}$S]GTPS activities in CHO cells in which human 5-HT$_{2c}$ receptors are transformed were measured.

Specifically, human CHO cells were suspended in 0.4% DMSO, and then the compound in Example 22 at various concentrations of 0.001, 0.01, 0.1, 1, and 10 M and the suspension were added to an incubation buffer containing 20 mM HEPES (pH 7.4), 100 mM NaCl, 10 mM MgCl2, and 1 mM EDTA, and incubated at 30° C. for 45 minutes. After incubation, inhibition rate of serotonin (5-HT)-induced [$^{35}$S] GTPS increase was calculated by measuring concentrations of bound [$^{35}$S]GTPS. From the results, compounds having more than 50% inhibition rate of serotonin (5-HT)-induced [$^{35}$S]GTPS increase were classified as antagonists. SB242084, a 5-HT$_{2c}$ antagonist, was used as a control group. Results are summarized in FIG. 1 and Table 4.

<Table 4, Inhibition Rate of Serotonin (5-HT)-Induced [$^{35}$S]GTPS of Compounds in Example 22>

TABLE 4

| Concentration (M) | Inhibition rate (%) |
|---|---|
| 0.001 | 0 |
| 0.01 | 1 |
| 0.1 | 9 |
| 1 | 67 |
| 10 | 100 |

As shown in FIG. 1 and Table 4, human 5-HT$_{2c}$ receptors exhibited a 5-HT concentration-dependent increase in [$^{35}$S] GTPS concentration levels with EC$_{50}$=0.02 M, and the increase in [$^{35}$S]GTPS concentration level was inhibited by SB242084, a 5-HT$_{2c}$ antagonist in Example 22. In particular, compounds in Example 22 according to the present invention inhibit 0, 1, 9, 67, and 100% in 30 M serotonin (5-HT)-induced GTP level increase at 0.001, 0.01, 0.1, 1, and 10 M, respectively, and showed a significant antagonist activity with IC$_{50}$=0.59 μM.

Thus, derivatives according to the present invention show a significant antagonist activity on human 5-HT$_{2c}$ receptors and may prevent or treat diseases caused by serotonin which is excessively bound to 5-HT$_{2c}$ receptors.

Piperidine derivatives represented by Formula (1) 1 according to the present invention may be formulated in various forms according to the intended purpose. Formulations containing the compounds represented by Formula (1) according to the present invention as an active ingredient are illustrated in the following examples, but are not construed to limit the scope of the invention.

Formulation Example 1

Pharmaceutical Formulations

<1-1> Tablet (Direct Compression)

After being sieved, 5.0 mg of a piperidine compound of Formula (1) was mixed with 14.1 mg of lactose, 0.8 mg of Crospovidone USNF, and 0.1 mg of magnesium stearate, and compressed into tablets.

<1-2> Tablet (Wetting Formulation)

After being sieved, 5.0 mg of a piperidine compound of Formula (1) was mixed with 16.0 mg of lactose and 4.0 mg of starch. To the resulting mixture, solution of 0.3 mg of polysolvate 80 in purified water was added, followed by granulation. Next, the resulting granules were dried, sieved, mixed with 2.7 mg of colloidal silicon dioxide and 2.0 mg of magnesium stearate, and compressed into tablets.

<1-3> Powder and Capsule 5.0 mg of an active ingredient was sieved and mixed with 14.8 mg of lactose, 10.0 mg of polyvinyl pyrrolidone, and 0.2 mg of magnesium stearate. The mixture was filled in a hard gelatine capsule No. 5, using a suitable apparatus.

<1-4> Injection Solution

An injection was prepared by mixing 100 mg of an active ingredient, 180 mg of mannitol, 26 mg of Na2HPO4-12H2O and 2974 mg of distilled water.

Formulation Example 2

Preparation of Food

<2-1> Preparation of Flour Food

Food for health improvement was prepared by adding the compound of Formula (1) according to the present invention by 0.5 to 5 weight % to wheat flour, and then making bread, cakes, cookies, crackers and noodles using the mixture.

<2-2> Preparation of Dairy Products

Various dairy products such as butter and ice cream were prepared by adding the compound of Formula (1) according to the present invention by 5 to 10 weight % to milk and using the mixture.

<2-3> Preparation of Sunsik (Grain Powder)

Brown rice, barley, glutinous rice and *coix* (job's tear) were gelatinized by the conventional method, followed by drying. The dried mixture was distributed and pulverized, resulting in 60-mesh size grain powders. Black bean, black sesame and *perilla* were steamed and dried by the conventional method. The dried mixture was distributed and pulverized, resulting in 60-mesh size grain powders. The compound of Formula (1) according to the present invention was vacuum-concentrated under reduced pressure using a vacuum concentrator, which was then spray-dried with a hot-air drier. The dried material was pulverized by a grinder, resulting in 60-mesh size grain powders. The prepared grain, seeds, and compound of Formula (1) according to the present invention were all mixed at the following ratio.

Grain (brown rice 30 weight %, coix 15 weight %, barley 20 weight %),

Seeds (perilla 7 weight %, black bean 8 weight %, black sesame 7 weight %),

Compound of Formula (1) (3 weight %),

*Ganoderma lucidum* (0.5 weight %),

*Rehmannia glutinosa* (0.5 weight %).

Manufacturing Example 3

Preparation of Beverages

<3-1> Preparation of Carbonated Beverages

Sugar (5 to 10%), citric acid (0.05 to 0.3%), caramel (0.005 to 0.02%), vitamin C (0.1 to 1%), and the compound of Formula (1) (1 to 5%) were mixed, to which purified water (79~94%) was added to make syrup. The prepared syrup was sterilized at 85 to 98° C. for 20 to 180 seconds, and mixed with cooling water at the ratio of 1:4. And then, carbon dioxide gas (0.5 to 0.82%) was given to the mixture to prepare carbonated beverages containing the compound of Formula (1) of the present invention.

<3-2> Preparation of Health Beverages

Liquid fruit sugar (0.5%), oligosaccharide (2%), sugar (2%), salt (0.5%) and water (75%) were all mixed with the compound of Formula (1) evenly, followed by sterilization. The mixture was put in a small container such as a glass bottle or PET bottle, resulting in health beverages.

<3-3> Preparation of Vegetable Juice 5 g of the compound of Formula (1) of the present invention was added to 1 l of tomato or carrot juice to prepare health vegetable juice.

<3-4> Preparation of Fruit Juice 1 g of the compound of Formula (1) of the present invention was added to 1 l of apple or grape juice to produce health fruit juice.

The present invention may be useful in new indole carboxylic acid bispyridyl carboxamide derivatives, preparation methods thereof, and preparation of compositions for prevention or treatment of obesity, urinary disorders, and CNS disorders, containing the same as an active ingredient. The present invention may be also useful in treatment or prevention of obesity; urinary disorders such as urinary incontinence, premature ejaculation, erectile dysfunction, and prostatic hyperplasia; CNS disorders such as depression, anxiety, concern, panic disorder, epilepsy, obsessive-compulsive disorder, migraine, sleep disorder, withdrawal from drug abuse, Alzheimer's disease, and schizophrenia, associated with 5-$HT_{2c}$ receptors.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As apparent from the above description, the present invention provides a new indole carboxylic acid bispyridyl carboxamide derivative, a preparation method thereof, and a composition for prevention or treatment of obesity, urinary disorders, and CNS disorders. Due to having high affinity for 5-$HT_{2c}$ receptors and selectivity on the 5-$HT_{2c}$ receptors, the indole carboxylic acid bispyridyl carboxamide derivatives according to the present invention are therapeutically effective for obesity; urinary disorders such as urinary incontinence, premature ejaculation, erectile dysfunction, and prostatic hyperplasia; CNS disorders such as depression, anxiety, concern, panic disorder, epilepsy, obsessive-compulsive disorder, migraine, sleep disorder, withdrawal from drug abuse, Alzheimer's disease, and schizophrenia, associated with 5-$HT_{2c}$ receptors.

The invention claimed is:
1. A compound represented by Formula (I), and pharmaceutically acceptable salts thereof:

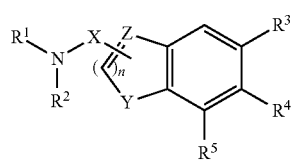

Formula (1)

wherein,
$R^1$ is

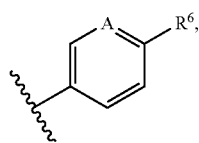

A is N,
$R^6$ is

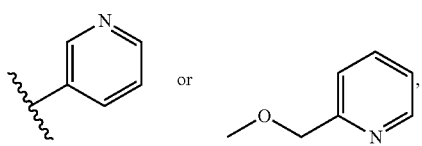

$R^2$ is H or a $C_1$ to $C_5$ linear or branched alkyl group,
$R^3$ to $R^5$ are independently or selectively H, a $C_1$ to $C_5$ alkyl group, a $C_1$ to $C_5$ alkoxy group, or halogen,
X is $CH_2$, C=O, C=S, or $SO_2$,
Y is O, S, NH, or N—$CH_3$,
Z is C or N, and
n is 1.

2. An indole compound selected from the group consisting of:
(1) benzofuran-3-sulfonic acid[6-(2-methyl-pyridine-3-yloxy)-pyridine-3-yl]-amide;
(2) benzo[b]thiophene-3-sulfonic acid[6-(2-methyl-pyridine-3-yloxy)-pyridine-3-yl]-amide;
(3) benzofuran-3-carboxylic acid[6-(2-methyl-pyridine-3-yloxy)-pyridine-3-yl]-amide;
(4) benzo[b]thiophene-3-carboxylic acid[6-(2-methyl-pyridine-3-yloxy)-pyridine-3-yl]-amide;
(5) 1H-indole-2-carboxylic acid[6-(2-methyl-pyridine-3-yloxy)-pyridine-3-yl]-amide;
(6) 1H-indole-3-carboxylic acid[6-(2-methyl-pyridine-3-yloxy)-pyridine-3-yl]-amide;
(7) 1H-benzoimidazole-2-carboxylic acid[6-(2-methyl-pyridine-3-yloxy)-pyridine-3-yl]-amide;
(9) (1H-indole-3-ylmethyl)-[6-(2-methyl-pyridine-3-yloxy)-pyridine-3-yl]-amine;
(10) 1H-indole-3-carbothioic acid[6-(2-methyl-pyridine-3-yloxy)-pyridine-3-yl]-amide;
(11) 1-methyl-1H-indole-3-carboxylic acid[6-(2-methyl-pyridine-3-yloxy)-pyridine-3-yl]-amide;
(12) 1H-indole-3-carboxylic acid methyl-[6-(2-methyl-pyridine-3-yloxy)-pyridine-3-yl]-amide;
(13) 1-methyl-1H-indole-3-carboxylic acid methyl-[6-(2-methyl-pyridine-3-yloxy)-pyridine-3-yl]-amide;
(14) 5-methyl-1H-indole-3-carboxylic acid[6-(2-methyl-pyridine-3-yloxy)-pyridine-3-yl]-amide;
(15) 5-methoxy-1H-indole-3-carboxylic acid[6-(2-methyl-pyridine-3-yloxy)-pyridine-3-yl]-amide;
(16) 6-methyl-1H-indole-3-carboxylic acid[6-(2-methyl-pyridine-3-yloxy)-pyridine-3-yl]-amide;
(17) 7-methyl-1H-indole-3-carboxylic acid[6-(2-methyl-pyridine-3-yloxy)-pyridine-3-yl]-amide;
(18) 5-iodo-1H-indole-3-carboxylic acid[6-(2-methyl-pyridine-3-yloxy)-pyridine-3-yl]-amide;
(19) 1H-indole-3-carboxylic acid[6-(pyrimidine-5-yloxy)-pyridine-3-yl]-amide;
(20) 1H-indole-3-carboxylic acid[6-(pyridine-2-yl-methoxy)-pyridine-3-yl]-amide;
(21) 1H-indole-3-carboxylic acid [6-(6-methyl-pyridine-3-yloxy)-pyridine-3-yl]-amide;
(22) 1H-indole-3-carboxylic acid [6-(2-chloro-pyridine-3-yloxy)-pyridine-3-yl]-amide;
(23) 1H-indole-3-carboxylic acid [6-(2-bromo-pyridine-3-yloxy)-pyridine-3-yl]-amide;
(24) 1H-indole-3-carboxylic acid [6-(pyridine-3-yloxy)-pyridine-3-yl]-amide;
(25) 1H-indole-3-carboxylic acid (6-phenoxy-pyridine-3-yl)-amide; and
(28) 6-methyl-1H-indole-3-carboxylic acid [6-(2-chloro-pyridine-3-yloxy)-pyridine-3-yl]-amide.

3. A method for preparing the compound of claim 1, wherein $R^2$ is H as represented by Chemistry FIG. 1a, comprising:
reacting a substituted heteroaryl derivative of Chemistry FIG. 2 with an amine compound of Chemistry FIG. 3 to prepare a compound of Chemistry FIG. 1, as described in Reaction Formula 1:

[Reaction Formula 1]

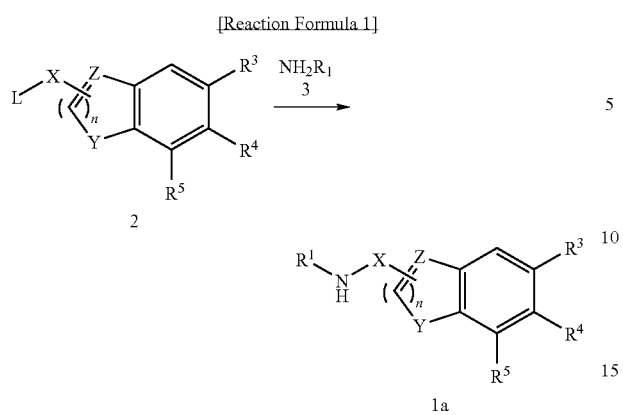

wherein $R^1$ to $R^5$, n, X, Y, and Z are as defined in Chemistry FIG. 1 of claim 1, and L is a leaving group.

4. The method according to claim 3, wherein, when the heteroaryl derivative (2) is a heteroaryl carboxylic acid derivative, the reaction is carried out in a reaction solvent in the presence of a condensing agent and a base at room temperature to the boiling temperature of the solvent.

5. The method according to claim 4, wherein the reaction solvent is one selected from the group consisting of tetrahydrofuran (THF), 1,4-dioxane, benzene, toluene, dichloromethane (DCM), chloroform, acetonitrile, and dimethylformamide (DMF), or a mixed solvent thereof.

6. The method according to claim 4, wherein the condensing agent is selected from the group consisting of N,N-carbonyldiimidazole (CDI), dicyclohexylcarbodiimide (DCC), diisopropylcarbodiimide (DIPC), 1-ethyl-3-(3-dimethylaminopropyl)carbodiimide (EDC), and O-(benzotriazol-1-yl)-N,N,N',N'-tetramethyluronium hexafluorophosphate (HBTU).

7. The method according to claim 4, wherein the base is selected from the group consisting of pyridine, diisopropylethylamine, triethylamine, and 1,8-diazabicyclo-[5.4.0]undec-7-ene (DBU).

8. The method according to claim 3, wherein, when the heteroaryl derivative (2) is a heteroarylsulfonyl derivative, the reaction is carried out in a reaction solvent in the presence of a base at room temperature.

9. The method according to claim 8, wherein the reaction solvent is one selected from the group consisting of tetrahydrofuran (THF), 1,4-dioxane, benzene, toluene, dichloromethane (DCM), chloroform, acetonitrile, and dimethylformamide (DMF), or a mixed solvent thereof.

10. The method according to claim 8, wherein the base is selected from the group consisting of pyridine, diisopropylethylamine, triethylamine, and 1,8-diazabicyclo-[5.4.0]undec-7-ene (DBU).

11. The method according to claim 3, further comprising introducing an alkyl group ($R^2$) into the amine, as described in Reaction Formula 4:

[Reaction Formula 4]

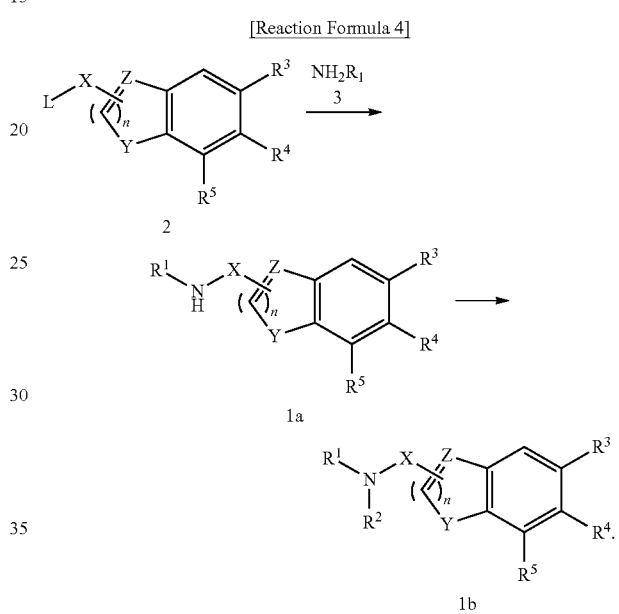

* * * * *